(12) United States Patent
Wang et al.

(10) Patent No.: US 10,316,335 B2
(45) Date of Patent: Jun. 11, 2019

(54) METHODS AND COMPOSITIONS FOR GENERATING STABLE TRANSFECTED CELLS

(71) Applicant: MaxCyte, Inc., Gaithersburg, MD (US)

(72) Inventors: Weili Wang, Gaithersburg, MD (US); James P. Brady, Gaithersburg, MD (US); Madhusudan V. Peshwa, Gaithersburg, MD (US)

(73) Assignee: MaxCyte, Inc., Gaithersburg, MD (US)

( * ) Notice: Subject to any disclaimer, the term of this patent is extended or adjusted under 35 U.S.C. 154(b) by 337 days.

(21) Appl. No.: 14/777,079

(22) PCT Filed: Mar. 14, 2014

(86) PCT No.: PCT/US2014/028561
§ 371 (c)(1),
(2) Date: Apr. 20, 2016

(87) PCT Pub. No.: WO2014/144237
PCT Pub. Date: Sep. 18, 2014

(65) Prior Publication Data
US 2016/0053283 A1    Feb. 25, 2016

Related U.S. Application Data

(60) Provisional application No. 61/794,785, filed on Mar. 15, 2013.

(51) Int. Cl.
*C12N 5/10*    (2006.01)
*C12N 15/87*   (2006.01)
*C12N 9/12*    (2006.01)

(52) U.S. Cl.
CPC .......... *C12N 15/87* (2013.01); *C12N 9/1205* (2013.01); *C12N 2510/02* (2013.01); *C12Y 207/01095* (2013.01)

(58) Field of Classification Search
None
See application file for complete search history.

(56) References Cited

U.S. PATENT DOCUMENTS

| | | |
|---|---|---|
| 4,554,101 A | 11/1985 | Hopp |
| 5,475,096 A | 12/1995 | Gold et al. |
| 5,570,163 A | 10/1996 | Yamauchi |
| 5,612,207 A | 3/1997 | Nicolau et al. |
| 5,720,921 A | 2/1998 | Meserol |
| 6,074,605 A | 6/2000 | Meserol et al. |
| 6,090,617 A | 6/2000 | Meserol |
| 6,485,961 B1 | 11/2002 | Meserol |
| 6,617,154 B1 | 9/2003 | Meserol |
| 6,773,669 B1 | 8/2004 | Holaday et al. |
| 7,029,916 B2 | 4/2006 | Dzekunov et al. |
| 7,141,425 B2 | 11/2006 | Dzekunov et al. |
| 7,186,559 B2 | 3/2007 | Dzekunov et al. |
| 7,771,984 B2 | 8/2010 | Dzekunov et al. |
| 2003/0032175 A1 | 2/2003 | Siebel et al. |
| 2004/0087025 A1 | 5/2004 | June et al. |
| 2004/0115784 A1 | 6/2004 | Dzekunov |
| 2004/0214333 A1 | 10/2004 | Liu et al. |
| 2005/0019311 A1 | 1/2005 | Holaday et al. |
| 2005/0282200 A1 | 12/2005 | Dzekunov et al. |
| 2006/0110793 A1 | 5/2006 | Goldenberg et al. |
| 2007/0059833 A1 | 3/2007 | Li et al. |
| 2008/0138877 A1 | 6/2008 | Dzekunov et al. |
| 2008/0311095 A1 | 12/2008 | Holmes et al. |
| 2011/0065171 A1 | 3/2011 | Dzekunov et al. |
| 2013/0326645 A1 | 12/2013 | Cost et al. |
| 2014/0065616 A1 | 3/2014 | Xu |
| 2016/0053283 A1 | 2/2016 | Wang et al. |

FOREIGN PATENT DOCUMENTS

| | | |
|---|---|---|
| JP | 2007/007430 | 1/2007 |
| JP | 2008/507300 | 3/2008 |
| JP | 2008/509653 | 3/2008 |
| WO | WO 1998/037757 | 9/1998 |
| WO | WO 2002/026966 | 4/2002 |
| WO | WO 2003/018751 | 3/2003 |
| WO | WO 2004/031353 | 4/2004 |
| WO | WO 2007/118208 | 10/2007 |
| WO | WO 2012/001073 | 1/2012 |
| WO | WO 2012/012738 | 1/2012 |
| WO | WO 2013/139994 | 9/2013 |
| WO | WO 2014/144237 | 9/2014 |
| WO | WO 2015/160683 | 10/2015 |

OTHER PUBLICATIONS

Edmonds et al.: "Development of Transfection and High-Producer Screening Protocols for the CHOK1SV Cell System", Molecular Biology, 34(2), (2006), pp. 179-190.
Derouazi et al.: "Serum-free large-scale transient transfection of CHO cells", Biotechnology and Bioengineering, 87(4), (2004), pp. 537-545.
Fan et al.: "Improving the efficiency of CHO cell line generation using glutamine synthetase gene knockout cells", Biotechnology and Bioengineering, 109(4), (2012), pp. 1007-1015.
Florea et al.: "Polyethyleneimine in Differentiated Calu-3 and Nondifferentiated COS-1 Cell Cultures", AAPS PharmSci., 4(3) Article 12, (2002), pp. 1-11.
International Search Report and Written Opinion issued in PCT/US2014/028561, dated Aug. 1, 2014.
Johansson et al.: "Yellow Fluorescent Protein-Based Assay to Measure GABAA Channel Activation and Allosteric Modulation in CHO-K1 Cells", PLoS ONE, 8(3): e59429, (2013), pp. 1-7.

(Continued)

*Primary Examiner* — Jennifer E Graser
(74) *Attorney, Agent, or Firm* — Norton Rose Fulbright US LLP

(57) ABSTRACT

Methods and compositions are provided involving high producing cell lines. Embodiments concern efficient methods for screening for such cell lines and for creating such cell lines. These cell lines can be used to create large amounts of protein. To quickly generate large quantity of recombinant proteins or vaccines for both pre-clinical study and clinical trials, almost all drug development will face the same challenging obstacle of rapidly generating a high stable producer. Developing and identifying a stable cell line is a critical part of biopharmaceutical development.

14 Claims, 9 Drawing Sheets

(56) References Cited

OTHER PUBLICATIONS

Nair et al.: "Effect of different UCOE-promoter combinations in creation of engineered cell lines for the production of Factor VIII", BMC Research Notes, 4:178, (2011), pp. 1-8.

Reisinger et al.: "Serum-free transfection of CHO cells with chemically defined transfection systems and investigation of their potential for transient and stable transfection", Cytotechnology, 60(1-3), (2009), pp. 115-123.

Tait et al.: "Transient production of recombinant proteins by Chinese hamster ovary cells using polyethylenimine/DNA complexes in combination with microtubule disrupting anti-mitotic agents", Biotechnology and Bioengineering, 88(6):707-21, (2004), pp. 1-15.

Steger et al., "CHO-S Antibody Titers >1 Gram/Liter Using Flow Electroporation-Mediated Transient Gene Expression followed by Rapid Migration to High-Yield Stable Cell Lines," *Journal of Biomolecular Screening* 2015; 20(4): 545-551.

Auer et al., "CRISPR/Cas9 and TALEN-mediated knock-in approaches in zebrafish," *Methods*, 69:142-150, (2014).

De Ravin et al., "Targeted gene addition in human CD34+ hematopoietic cells for correction of X-linked chronic granulomatous disease," *Nature Biotechnology*, 34(4):424-431, (2016).

Field et al., "Comparison of Lentiviral and Sleeping Beauty Mediated $\alpha\beta$ T Cell Receptor Gene Tranfer," *PLOS One*, 8(6):e68201, (2013).

Field et al., "Engineered T Cell Therapies," *Expert Review in Molecular Medicine*, vol. 17, (2015).

Genovese et al., "Targeted Genome Editing in Human Repopulating Hematopoietic Stem Cells," *Nature*, 510(7504):235-240, (2014).

Hashimoto et al., "electroporation of Cas9 protein/sgRNA into early pronuclear zygotes generates non-mosaic mutants in the mouse," *Developmental Biology*, 418:1-9, (2016).

International Search Report and Written Opinion issued in International Application No. PCT/US2016/027253, dated Jun. 16, 2016.

International Search Report and Written Opinion issued in International Application No. PCT/IB17/54446, dated Jan. 4, 2018.

International Search Report and Written Opinion issued in International Patent Application No. PCT/US2015/025523, dated Jul. 21, 2015.

Kim et al., "Highly efficient RNA-guided genome editing in human cells via delivery of purified Cas9 ribonucleoproteins," *Genome Research*, 24:1012-1019, (2014).

Li et al., "Genomic Editing of Human Hematopoietic Stem Cells Using Non-Viral, Clinical Scale cGMP Platform and Messenger RNA (mRNA) Encoding Nucleases," *Molecular Therapy*, 22(1):S278, (2014).

Lin et al., "Enhanced homology-directed human genome engineering by controlled timing of CRISPR/Cas9 delivery," *eLIFE*, 3:e04766, (2014).

Ma et al., "Effect of Sodium Butyrate and propionate on Cell Growth, Metabolism and Expression of the Chimeric Antibody," *China Biotechnology*, 2005, 25(10): 12-16. (English Abstract).

Musunuru, "Genome editing of human pluripotent stem cells to generate human cellular disease models," *Disease Models & Mechanisms*, 6(4): 896-904, (2013).

Novak et al., "In Vitro Transfection of Fresh Thymocytes and T Cells Shows Subset-Specific Expression of Viral Promoters," *Molecular and Cellular Biology*, 12(4):1515-1527, (1992).

Office Action issued in Chinese Patent Application No. 201480021503. 5, dated Apr. 20, 2018.

Osborn et al., "Evaluation of TCR Gene Editing Achieved by TALENs, CRISPR/Cas9, and MegaTAL Nucleases," *Molecular Therapy*, 24(3):570-581, (2016).

Palin et al., "Human Neonatal Naive CD4+ T Cells have Enhanced Activation-Dependent Signaling Regulated by the MicroRNA miR-181a," *The Journal of Immunology*, 19:2682-2691, (2013).

Ramos et al., "Chimeric Antigen Receptor (CAR)-Engineered Lymphocytes for Cancer Therapy," *Expert. Opin. BIol. Ther.*, 11(7):855-873, (2011).

Ran et al., "Genome engineering using the CRISPR-Cas9 System," *Nature Protocols*, 8(11):2281-2308, (2013).

Rong et al., "Homologous recombination in human embryonic stem cells using CRISPR/Cas9 nickase and a long DNA donor template," *Protein Cell*, 5(4):258-260, (2014).

Schumann et al., "Generation of Knock-in primary human T cells using Cas9 ribonucleoproteins," *PNAS*, 112(33):10437-10442, (2015).

Wang et al., "Establishment of leukocyte-associated immunoglobulin like-receptor 2 (CD306) eukaryotic expression vector and purification and identification of fusion protein," *Journal of Clinical Rehabilitative Tissue Engineering Research*, 2009, 13(50):9928-9932. (English Abstract).

Wang et al., "Highly efficient homology-driven genome editing in human T cells by combining zing-finger nuclease mRNA and AAV6 donor delivery," *Nucleic Acids Research*, 44(3):e30, (2015).

Wurm, "Production of recombinant protein therapeutics in cultivated mammalian cells," *Nature Biotechnology*, 2004, 22(11): 1393-1398.

Yang et al., "Construction of Anti-VEGFR-2 scFv-Fc Fusion Antibody and Stable Expression in CHO-k Cells," *Pharmaceutical Biotechnology*, 2011, 18(3):206-210. (English Abstract).

Zhang et al., "Biallelic targeting of expressed genes in mouse embryonic stem cells using the Cas9 system," *Methods*, 69(2):171-178, (2014).

Zhao et al., "High transfection efficiency of porcine peripheral blood T cells via nucleofection," *Veterinary Immunology and Immunopathology*, 144:179-186, (2011).

Office Action in Corresponding Japanese Application No. 2016/502834, dated Feb. 28, 2018 (English translation).

| conditions | DNA | DNA] | TKN protocol | TKN cell No. | [G418] | Viability @ day8 | Viability @ day14 |
|---|---|---|---|---|---|---|---|
| Sample 1 | Circular | 200 ug/ml | CHO2 | 80E6 | 0.8 g/L | 28 % | NS |
| Sample 2 | Circular | 200 ug/ml | CHO2 | 80E6 | 1.6 g/L | 8% | NS |
| Sample 3 | Circular | 400 ug/ml | CHO2 | 80E6 | 0.8 g/L | 66% | 21% |
| Sample 4 | Circular | 400 ug/ml | CHO2 | 80E6 | 1.6 g/L | 61% → 23%* | |
| Sample 5 | Linearized | 200 ug/ml | CHO2 | 80E6 | 0.8 g/L | 22% | NS |
| Sample 6 | Linearized | 200 ug/ml | CHO2 | 80E6 | 1.6 g/L | 8% | NS |
| Sample 7 | Linearized | 400 ug/ml | CHO2 | 80E6 | 0.8 g/L | 29% | 29% |
| Sample 8 | Linearized | 400 ug/ml | CHO2 | 80E6 | 1.6 g/L | 10% → 50%* | |
| Sample 9 As a control | No DNA | x | CHO2 | 80E6 | 0.8 g/L | 0% | x |

FIG. 9

METHODS AND COMPOSITIONS FOR GENERATING STABLE TRANSFECTED CELLS

CROSS-REFERENCE TO RELATED APPLICATIONS

This Application is a national phase application under 35 U.S.C § 371 of International Application No. PCT/US2014/028561, filed Mar. 14, 2014, and claims priority to U.S. Provisional Patent Application Ser. No. 61/794,785, filed on Mar. 15, 2013. The entire contents of each of the above-referenced disclosures are hereby incorporated by reference.

BACKGROUND OF THE INVENTION

1. Field of the Invention

The present invention relates generally to the field of biotechnology. More particularly, it concerns novel methods and compositions for the generation of stable transfected cells.

2. Description of Related Art

To quickly generate large quantity of recombinant proteins or vaccines for both pre-clinical study and clinical trials, almost all drug development will face the same challenging obstacle of rapidly generating a high stable producer. Developing and identifying a stable cell line is a critical part of biopharmaceutical development. However, stable cell line development is a complicated process usually including transfection, selection, cloning/screening, comparison study, characterization and stability studies. Transfection is the first step of the process that will determine whether a stable cell line with high titer and good product quality can be generated within the required timeline. Many existing transfection methods have shown low transfection efficiency, like PEI and lipid methods, or low cell viability with moderate transfection efficiency with other EP methods (Tait 2004; Derouazi 2004; Reisinger 2009; Florea 2002). These two limiting factors resulted in the need of tedious, elaborate, time-consuming, and resource-intensive selection process. Commonly, several thousand clones will be screened to identify a good stable clone (Dharshanan 2011; Shi 2011) and expansive automation systems for both liquid handling and clone pick/selection such as Ambr™ system, ClonePix, FACS sorting and SimCell system (Dharshanan 2011; Shi 2011; Moses 2012; Lindgren 2009; Sleiman 2008; Carroll 2004; Thomas 2008) are invested and used by many pharmaceutical companies in this field. Others have also developed specific proprietary expression vectors and cell lines to generate high-yield stable cell line (de la Cruz 2006; Fan 2012; Nair 2011).

SUMMARY OF THE INVENTION

Compositions and methods concern stable cell lines that produce exogenous protein or gene product including high producing cell lines. Such cell lines can be produced and identified using very high concentrations of antibiotic—i.e., concentration levels that would typically kill a cell even if it were transfected with a gene conferring resistance to the antibiotic). Embodiments involve the use of culture conditions that include a "conditionally lethal concentration" of the selection agent, which refers to a concentration level of the selection agent (e.g., antibody) that would kill at least 10% more cells when comparing the viability percentages of untransfected cells versus transfected cells after at least 6 days of incubation in that concentration.

Therefore, in some embodiments there are methods for producing a stable cell line that expresses an exogenous polypeptide, complex assembly of polypeptides (e.g., Virus-Like Particles, VLPs) or complex assembly of nucleotides and other molecules (e.g. gene therapy viral vectors such as lentivirus, adenovirus, or adeno-associated virus), the method comprising transfecting an expression construct into cells using electroporation, wherein the expression construct comprises i) a selectable gene and ii) a sequence encoding one or more exogenous polypeptides either themselves or along with other molecules; and selecting for expression of selectable gene under culture conditions comprising a conditionally lethal concentration of the selection agent. Delivering nucleic acids into a cell using electroporation is used in methods described herein. Steps include electroporating the cells with the desired nucleic acid such that one or more nucleic acid molecules is taken into the cell.

The term "exogenous polypeptide" refers to a polypeptide encoded by a nucleotide sequence of which all or part of the sequence was introduced into the cell originally by a transfection procedure discussed herein. Of course, cells expressing an exogenous polypeptide may be the progeny of a parent cell that had been transfected with exogenous sequence. For example, a cell may be transfected with an expression construct that provides expression for a polypeptide either not expressed from the genome of the cell prior to transfection or already expressed by the cell (but the cell has increased production capability following expression from the transfected nucleic acid). In some embodiments, the cell may produce a version of a polypeptide (endogenous polypeptide) and the exogenous polypeptide may be an altered version of that polypeptide. In one embodiment, the altered version is a wild-type version of the polypeptide. In another embodiment, the altered version is a truncated version of the endogenous polypeptide that might act, for instance, as a decoy. In other embodiments, an exogenous gene product may be produced that is not limited only to polypeptides. An exogenous polypeptide may be produced in conjunction with an exogenous gene product, that is, an RNA transcript that does not encode a polypeptide but is functional as an RNA molecule. The RNA molecule may be an RNAi, siRNA, miRNA, mRNA, or other RNA molecule.

In certain embodiments, cells are electroporated using flow electroporation. Flow electroporation, which refers to a process, comprising: transferring a suspension of cells and loading molecules into an apparatus comprised of a fluid chamber or fluid flow path; the said fluid chamber or fluid flow path being comprised of electrodes disposed along sides of the fluid chamber or fluid flow path and configured to subject biological particles within the fluid chamber fluid flow path to an electric field suitable for electroporation; and transferring the electroporated cell suspension out of the apparatus. This method is particularly effective for large scale volume of cells. Static electroporation, by contrast, involves electroporation of a set and limited volume of cells due to constraints associated with moving electricity across liquid and the distance between opposing electrodes.

An "expression construct" is a nucleotide sequence encoding for a desired gene or sequence to be expressed within a target cell. An expression construct for use with the disclosed methods and compositions may be, for example, an oligonucleotide sequence, DNA molecule, RNA molecule, bacterial plasmid, chromosomal gene editing systems (e.g., nuclease, integrase, transposon/transposase, TALENs, CRISPR/Cas9 and guide sequence) viral vector, virus, cosmid, artificial chromosome. In particular aspects, the expression construct is a bacterial plasmid. In certain embodiments, the expression construct is circular. In other embodiments, the expression construct is linear. In some embodiments the expression construct is DNA, though it may also be RNA. In most cases, the expression construct is double-stranded, but in some embodiments, the expression construct may be single-stranded or comprise a single-stranded region.

The cells that are transfected with an expression construct may be any suitable cells known to one of ordinary skill in the art, such as mammalian cells. In certain aspects, the cells are mammalian or insect cells. Suitable mammalian cells include, but are not limited to, CHO cells.

In certain aspects, transfecting the expression construct into cells comprises flowing a suspension of the cells through an electric field in a flow chamber, the electric field being produced by opposing oppositely charged electrodes at least partially defining the flow chamber, wherein thermal resistance of the flow chamber is less than approximately 10° C. per Watt. In other certain aspects transfecting the cells comprises employing a flow electroporation device comprising a chamber for containing a suspension of cells to be electroporated; the chamber being at least partially defined by opposing oppositely chargeable electrodes; and wherein the thermal resistance of the chamber is less than approximately 10° C. per Watt.

In some embodiments, transfecting the cells comprises employing a flow electroporation device comprising: walls defining a flow channel having an electroporation zone configured to receive and to transiently contain a continuous flow of a suspension of cells to be electroporated; an inlet flow portal in fluid communication with the flow channel, whereby the suspension can be introduced into the flow channel through the inlet flow portal; an outlet flow portal in fluid communication with the flow channel, whereby the suspension can be withdrawn from the flow channel through the outlet portal; the walls defining the flow channel within the electroporation zone comprising a first electrode forming a substantial portion of a first wall of the flow channel and a second electrode forming a substantial portion of a second wall of the flow channel opposite the first wall, the first and second electrodes being such that when placed in electrical communication with a source of electrical energy an electric field is formed therebetween through which the suspension can flow; and wherein the thermal resistance of the flow channel is less than approximately 10° C. per Watt. In certain such embodiments, the first and second electrodes are spaced from each other at least 1 mm. Moreover, the flow chamber may have a ratio of combined electrode surface in contact with buffer to the distance between the electrodes of approximately 1 to 100 cm. In particular embodiments, the flow chamber may have a ratio of combined electrode surface in contact with buffer to the distance between the electrodes of approximately 1 to 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100 cm, or any value derivable therein. In certain embodiments, the cells electroporated in the flow channel are not substantially thermally degraded thereby.

In some aspects, the flow electroporation device comprises a flow chamber for containing a suspension of cells to be electroporated; the flow chamber being at least partially defined by opposing oppositely chargeable electrodes; and wherein the flow chamber has a ratio of combined electrode surface in contact with buffer to the distance between the electrodes of approximately 1 to 100 cm. In particular aspects, the ratio is approximately 1 to 70 cm. In other particular aspects, the ratio is approximately 1 to 50 cm. For example, the ratio may be approximately 1 to 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100 cm, or any value derivable therein.

In some embodiments, the flow electroporation device comprises walls defining a flow channel configured to receive and to transiently contain a continuous flow of a suspension of cells to be electroporated; an inlet flow portal in fluid communication with the flow channel, whereby the suspension can be introduced into the flow channel through the inlet flow portal; an outlet flow portal in fluid communication with the flow channel, whereby the suspension can be withdrawn from the flow channel through the outlet portal; the walls defining the flow channel comprising a first electrode forming at least a portion of a first wall of the flow channel and a second electrode forming at least a portion of a second wall of the flow channel opposite the first wall, the first and second electrodes being such that when placed in electrical communication with a source of electrical energy an electric field is formed therebetween through which the suspension can flow; and wherein the thermal resistance of the flow channel is less than approximately 10° C. per Watt. In certain aspects, the thermal resistance of the flow channel is approximately 0.1° C. per Watt to 10° C. per Watt. For example, the thermal resistance of the flow channel may be approximately 0.1, 0.2, 0.3, 0.4, 0.5, 0.6, 0.7, 0.8, 0.9, 1.0, 1.5, 2.0, 2.5, 3.0, 3.5, 4.0, 4.5, 5.0, 5.5, 6.0, 6.5, 7.0, 7.5, 8.0, 8.5, 9.0, 9.5, or 10° C. per Watt, or any thermal resistance derivable therein. The first and second electrodes may be spaced from each other at least 1 mm, at least 2 mm, at least 3 mm, or any distance derivable therein. In any of the disclosed embodiments, the flow chamber may have a ratio of combined electrode surface in contact with buffer to the distance between the electrodes of approximately 1 to 100 cm. For example, the ratio may be approximately 1 to 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100 cm, or any value derivable therein. In certain aspects, the flow chamber has a ratio of combined electrode surface in contact with buffer to the distance between the electrodes of approximately 1 to 100 cm, and the first and second electrodes are spaced from each other at least 1 mm. In other aspects, the flow chamber has a ratio of combined electrode surface in contact with buffer to the distance between the electrodes of approximately 1 to 100 cm, and the first and second electrodes are spaced from each other at least 3 mm. In even further aspects, the flow chamber has a ratio of combined electrode surface in contact with buffer to the distance between the electrodes of approximately 1 to 100 cm, and the first and second electrodes are spaced from each other approximately 3 mm to approximately 2 cm. For example, the first and second electrodes may be spaced from each other approximately 3, 4, 5, 6, 7, 8, 9, or 10 mm, or any distance derivable therein, or the first and second electrodes may be spaced from each other approximately 1.0, 1.1, 1.2, 1.3, 1.4, 1.5, 1.6, 1.7, 1.8, 1.9, or 2.0 cm, or any distance derivable therein. In some aspects of these embodiments, the cells electroporated in the flow channel are not substantially thermally degraded thereby.

In certain disclosed methods and devices, the thermal resistance of the chamber is approximately 0.1° C. per Watt to approximately 4° C. per Watt. In some aspects, the thermal resistance of the chamber is approximately 1.5° C. per Watt to approximately 2.5° C. per Watt. For example, the thermal resistance of the chamber may be approximately 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, or 4.0° C. per Watt, or any resistance derivable therein.

In certain disclosed methods and devices, the flow electroporation device comprises: walls defining a flow channel configured to receive and to transiently contain a continuous flow of a suspension comprising particles; an inlet flow portal in fluid communication with the flow channel, whereby the suspension can be introduced into the flow channel through the inlet flow portal; an outlet flow portal in fluid communication with the flow channel, whereby the suspension can be withdrawn from the flow channel through the outlet flow portal; the walls defining the flow channel comprising a first electrode plate forming a first wall of the flow channel and a second electrode plate forming a second wall of the flow channel opposite the first wall; wherein the area of the electrodes contact with the suspension, and the distance between the electrodes is chosen so that the thermal resistance of the flow channel is less than approximately 4° C. per Watt; the paired electrodes placed in electrical communication with a source of electrical energy, whereby an electrical field is formed between the electrodes; whereby the suspension of the particles flowing through the flow channel can be subjected to an electrical field formed between the electrodes. In certain aspects, the electrode plates defining the flow channel further comprise a gasket formed from an electrically non-conductive material and disposed between the first and second electrode plates to maintain the electrode plates in spaced-apart relation, the gasket defining a channel therein forming opposed side walls of the flow channel. The gasket may, for example, form a seal with each of the first and second electrode plates. In some embodiments, the device comprises a plurality of flow channels, and the gasket comprises a plurality of channels forming opposed side walls of each of the plurality of channels. In some aspects, one of the inlet flow portal and the outlet flow portal comprises a bore formed in one of the electrode plates and in fluid communication with the flow channel. The other of the inlet flow portal and the outlet flow portal may comprise a bore formed in the one of the electrode plates and in fluid communication with the flow channel. In certain aspects, the inlet flow portal and the outlet flow portal comprise a bore formed in the other of the electrode plates and in fluid communication with the flow channel. In any of the disclosed embodiments, the device may further comprise a cooling element operatively associated with the flow channel to dissipate heat. For example, the cooling element may comprise a thermoelectric cooling element. As another example, the cooling element may comprise a cooling fluid flowing in contact with the electrode. As yet another example, the cooling element may comprise a heat sink operatively associated with the electrode. The heat resistance of the flow channel may be less than approximately 3° C. per Watt. In some embodiments, the heat resistance of the flow channel is between approximately 0.5° C. per Watt and 4° C. per Watt, or the heat resistance of the flow channel is between approximately 1° C. per Watt and 3° C. per Watt. For example, the heat resistance of the flow channel may be approximately 0.5, 0.6, 0.7, 0.8, 0.9, 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, or 4.0° C. per Watt, or any value derivable therein.

In certain disclosed methods and devices, the first electrode may comprise an elongated, electrically conductive structure, wherein the second electrode comprises a tubular, electrically conductive structure; wherein the electrodes are concentrically arranged such that the second, tubular electrode surrounds the first electrode in spaced-apart relation thereto; and wherein the flow channel is disposed within an annular space defined between the first and second electrodes. The electrodes may form at least a portion of the walls defining the flow channel. In some embodiments, concentric annular spacers for maintaining the first and second electrodes are in spaced-apart, concentric relation. In certain aspects, the device is arranged in series or in parallel with a second, like device.

In certain methods involving transfecting cells by flow electroporation, the flow channel has a thermal resistance of less than approximately 10° C. per Watt. In some methods involving transfecting the cells by flow electroporation, the method involves flowing a suspension of cells to be electroporated through a flow channel and exposing the suspension of to an electric field while flowing through the flow channel, the electric field having a strength of greater than 0.5 kV/cm. For example, the electric field may have a strength of greater than approximately 3.5 kV/cm. In certain aspects the electric field has a strength of greater than approximately 0.5, 1.0, 1.5, 2.0, 2.5, 3.0, or 3.5 kV/cm, or any value derivable therein.

In certain methods involving transfection by electroporation, greater than 50% of the cells transfected by electroporation express the exogenous polypeptide. For example, approximately 50% to 95% of the cells transfected by electroporation express the exogenous polypeptide. As another example, approximately 60% to 90% of the cells transfected by electroporation express the exogenous polypeptide. As yet another example, approximately 70% to 80% of the cells transfected by flow electroporation express the exogenous polypeptide. In some particular aspects, approximately 50, 55, 60, 65, 70, 75, 80, 85, 90, 95, or 100%, or any percentage derivable therein, of the cells transfected by electroporation express the exogenous polypeptide.

In any of the disclosed methods, the cells transfected by flow electroporation may be greater than approximately 50% viable before and/or after selection. In certain aspects, the cells transfected by flow electroporation are greater than approximately 60%, 70%, 80%, or 90% viable before and/or after selection. In other certain aspects, the cells transfected by flow electroporation are approximately 50% to 90% viable before and/or after selection. In yet other aspects, the cells transfected by flow electroporation are approximately 60% to 90% viable before and/or after selection. For example, the cells transfected by flow electroporation may be greater than approximately 50, 55, 60, 65, 70, 75, 80, 85, 90%, or any percentage derivable therein, viable before and/or after selection.

Any of the disclosed methods may include a step employing limiting dilution of the selected transfected cells to obtain single cell colonies. As used herein, the term "limiting dilution" refers to the process of significantly diluting a cell culture, with the goal of achieving a single cell in each culture. When such an isolated, single cell reproduces, the resulting culture will contain only clones of the original cell. For example, a multi-well plate may be used to obtain single cell cultures or colonies.

In any of the disclosed methods involving selecting for the expression of a selection gene, the selection may occur in batch or suspension culture conditions. Any selection genes and selection agents known to those of skill in the art may be used in the disclosed methods. In certain aspects, the selection gene is an antibiotic resistance gene, and the selection agent is an antibiotic. For example, the antibiotic resistance gene may confer resistance to neomycin, puromycin, zeocin, G418, hygromycin, phleomycin or blasticidin. In particular embodiments, the antibiotic resistance gene confers resistance to neomycin, and the selection agent may be G418 or a derivative thereof.

In certain aspects, selection genes that can be controlled by specific nutrients or additives that can be supplemented or removed from cell culture medium are useful in the methods described herein. In certain aspects, the selection gene can be a gene that is directly or indirectly pharmacologically controlled in physical, chemical or biological agents. For example, DHFR (dihydrofolate reductase)-minus cells can be made by deleting or mutating the DHFR gene. Cells that lack DHFR require certain nutrients to grow, such as, for example, hypoxanthine, aminopterin, thymidine glycine, and glutamine. The DHFR gene can be used as a marker, and cells can be selected for expression of DHFR by excluding nutrients that DHFR-minus cells require to grow. A further example is the glutamine synthetase (GS) selection system. In cells that do not express a sufficient amount of GS, the GS gene can be used as a selection marker by plating on glutamine-free medium. Alternatively, a GS inhibitor, methionine sulphoximine (MSX), can be used to inhibit endogenous GS activity, such that only transfectants with additional GS activity can survive.

In further embodiments, it is specifically contemplated that selection systems that do not require the addition of a selective agent for the survival of transfected cells are excluded.

In methods where an antibiotic is used as a selection method, the transfected cells may be cultured with the antibiotic at a conditionally lethal concentration for at least 4 to 21 days. In some aspects, the transfected cells are cultured with the antibiotic at a conditionally lethal concentration for 4 to 10 days. For example, the transfected cells may be cultured with the antibiotic at a conditionally lethal concentration for 4, 5, 6, 7, 8, 9, 10, 11, 12, 13, 14, 15, 16, 17, 18, 19, 20, or 21 days, or any length of time derivable therein.

In methods where cells are cultured with an antibiotic at a conditionally lethal concentration, the cells may be maintained in culture having a lower concentration of the antibiotic after the culturing with the antibiotic at the conditionally lethal concentration. For example, the lower concentration of the antibiotic may be about 10% to 90% of the conditionally lethal concentration. As another example, the lower concentration of the antibiotic may be about 50% of the conditionally lethal concentration. In certain embodiments, the lower concentration of the antibiotic may be about 10, 15, 20, 25, 30, 35, 40, 45, 50, 55, 60, 65, 70, 75, 80, 85 or 90%, or any percentage derivable therein, of the conditionally lethal concentration. In any such methods where the cells are maintained in a culture having a lower concentration of the antibiotic as compared to the conditionally lethal concentration of antibiotic, the cells may be maintained at the lower concentration for 3 to 20 days. For example, the cells may be maintained at the lower concentration for approximately 3, 4, 5, 6, 7, 8, 9, 10, 11, 12, 13, 14, 15, 16, 17, 18, 19, or 20 days, or any time derivable therein, When cells are maintained at a lower concentration of the antibiotic as compared to the conditionally lethal concentration of antibiotic, the cells may be maintained at the lower concentration prior to cloning stable transfected cells using limiting dilution. As used herein, the term "cloning" refers to the process of producing a population of genetically identical cells (or substantially genetically identical cells) by replicating a single progenitor cell (which may be referred to as a "clonal").

In any of the disclosed methods, a step may be employed comprising expanding a clonal isolated and selected cell to produce clonal cells expressing the exogenous polypeptide. In some aspects, the clonal isolated cell is expanded in media comprising an antibiotic. For example, the concentration of the antibiotic during expansion may be no more than 50% of the conditionally lethal concentration of the antibiotic. As another example, the concentration of the antibiotic during expansion may be no more than 25% of the conditionally lethal concentration of the antibiotic. In certain aspects, the concentration of the antibiotic during expansion is no more than 25, 30, 35, 40, 45, or 50%, or any percentage derivable therein, of the conditionally lethal concentration of the antibiotic.

In disclosed methods involving the expansion of a clonal isolated cell, the expansion may be for large scale manufacturing. For example, the cells may be expanded in a volume of greater than 1 L, or the cells may be expanded in a volume of greater than 3 L. In certain aspects, the cells are expanded in a volume of greater than 1.0, 1.5, 2.0, 2.5, or 3.0 L, or any value derivable therein. The cells may be expanded in media comprising an antibiotic, and such media may include a conditionally lethal concentration of the antibiotic.

In any of the disclosed methods, the cells may be cultured in serum-free media. In some methods, an additional step is employed comprising isolating or purifying the exogenous polypeptide produced by the cells.

In certain aspects, the selected cells produce at least about 0.1 g/L, 0.5 g/L, 1.0 g/L, 1.5 g/L, 2 g/L, or 3 g/L of exogenous polypeptide. For example, the selected cells produce at least about 0.1, 0.2, 0.3, 0.4, 0.5, 0.6, 0.7, 0.8, 0.9. 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, or 3.0 g/L of exogenous peptide, or any range derivable therein. In other aspects, the selected cells produce at least about 0.1, 0.2, 0.3, 0.4, 0.5, 0.6, 0.7, 0.8, 0.9. 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, or 3.0 g/L of exogenous peptide (or any range derivable therein) within 5, 6, 7, 8, 9, 10, 11, or 12 weeks of being transfected (or any range derivable therein). In particular aspects, expanded clonal cells produce at least about 0.1 g/L, 0.5 g/L, 1.0 g/L, 1.5 g/L, 2 g/L, or 3 g/L of exogenous polypeptide (or any range derivable therein) within 6, 7, 8, 9, or 10 weeks of being transfected (or any range derivable therein). In other particular aspects, expanded clonal cells produce at least about 0.1, 0.2, 0.3, 0.4, 0.5, 0.6, 0.7, 0.8, 0.9. 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, or 3.0 g/L (or any range derivable therein) within 5, 6, 7, 8, 9, 10, 11, or 12 weeks of being transfected (or any range derivable therein). In even other aspects, expanded clonal cells produce greater than 10, 15, 20, 25, 30, 35, 40, 45, 50, 55, 60, 65, 70, 75, or 80 picograms of exogenous protein per cell per day (or any range derivable therein) within 6, 7, 8, 9, or 10 weeks of being transfected (or any range derivable therein).

In some embodiments, expanded clonal cells produce greater than 10% more protein per cell per day compared to control cells, wherein control cells are similar transfected cells but incubated with a concentration of antibiotic no more than 50% of a conditionally lethal concentration. In other embodiments, expanded clonal cells produce greater than about 20, 25, 30, 35, 40, 45, or 50% (or any percentage derivable therein) more protein per cell per day as compared to control cells, wherein control cells are similar transfected cells but incubated with a concentration of antibiotic no more than 50% of a conditionally lethal concentration. In certain methods, the transfected cells produce a level of the exogenous protein after generation 60 that is at least 50% the level of exogenous protein between generation 10 and 20.

In any of the disclosed methods, a further step may be employed comprising freezing transfected and selected cells. An even further step may also be employed, wherein previously frozen transfected and selected cells are expanded.

In some aspects, wherein the cells that are transfected and subject to selection are CHO cells, wherein the selection gene is neomycin, and the selection agent is G418 or a derivative thereof. In certain of such aspects involving CHO cells, the conditionally lethal concentration of G418 or derivative thereof is at least about 0.8 mg/ml. In other aspects involving CHO cells, the conditionally lethal concentration of G418 or derivative thereof is greater than about 1.0 mg/ml. For example, the conditionally lethal concentration of G418 or derivative thereof may be at least about or at most about 0.3, 0.4, 0.5, 0.6, 0.7, 0.8, 0.9, 1.0, 1.1, 1.2, 1.3, 1.4, 1.5, 1.6, 1.7, 1.8, 1.9, 2.0, 2.5, 3.0, 3.5, or 4 mg/ml, or any value derivable therein. In any such disclosed methods involving CHO cells, the selection agent may be G418.

In the disclosed methods, a conditionally lethal concentration of selection agent may be chosen based on the particular selection agent that is used, as would be understood by one of ordinary skill in the art. For example, a conditionally lethal concentration of G418 or derivative thereof may be greater than about 1.0 mg/ml. As another example, a conditionally lethal concentration of G418 or derivative thereof is greater than about 1.6 mg/ml. In certain aspects, the conditionally lethal concentration of G418 or derivative thereof is greater than about 1.0, 1.1, 1.2, 1.3, 1.4, 1.5, 1.6, 1.7, 1.8, 1.9, 2.0, 2.5, 3.0, 3.5, 4.0, 4.5, or 5 mg/ml, or any value derivable therein. In any disclosed methods involving an antibiotic as a selection agent, the antibiotic may be G418.

There are disclosed other methods for producing a stable CHO cell expressing line comprising: a) transfecting into CHO cells an expression construct comprising a sequence i) encoding a polypeptide conferring G418 resistance and ii) encoding one or more exogenous polypeptide using a flow electroporation device; b) selecting transfected CHO cells in media comprising greater than about 1.6 mg/ml of G418; c) isolating selected transfected CHO cells by limiting dilution to obtain clonal cells; and, d) expanding isolated transfected CHO cells to produce a stable CHO cell expressing line.

In the disclosed methods, the cell culture may include any additional ingredients known to those of ordinary skill in the art, as would be readily selected by those of ordinary skill in the art based on the type of cell that is cultured. For example, the cells may be cultured in sodium butyrate or comparable salt.

In the disclosed methods, a further step may be employed comprising expanding a clonal isolated and selected cell to produce clonal cells expressing the exogenous polypeptide.

Other embodiments concern methods for producing a stable CHO cell expressing line comprising: a) transfecting into CHO cells an expression construct comprising a sequence i) encoding a polypeptide conferring G418 resistance and ii) encoding one or more exogenous polypeptides using an electroporation device; b) selecting transfected CHO cells in media comprising greater than about 1.6 mg/ml of G418; c) isolating selected transfected CHO cells by limiting dilution to obtain clonal cells; and, d) expanding isolated transfected CHO cells to produce a stable CHO cell expressing line. In a specific embodiment, the electroporation device is a flow electroporation device. Such methods may further comprise collecting exogenous polypeptide produced by the replicated, transfected CHO cells. In certain methods concerning producing a stable CHO cell expressing line, the transfected cells are maintained in media comprising 1.6 mg/ml G418 for at least 6 days. In certain methods, the stable CHO cell expressing line produces more than about 2 g/L of exogenous protein in the media.

Additional embodiments concern methods for screening for high producing CHO cell lines comprising: a) transfecting into CHO cells an expression construct comprising a sequence i) encoding a polypeptide conferring G418 resistance and ii) encoding one or more exogenous polypeptides using an electroporation device; b) selecting transfected CHO cells in media comprising greater than about 1.6 mg/ml of G418 for at least 6 days; c) isolating selected transfected CHO cells by limiting dilution to obtain clonal cells; d) expanding isolated transfected CHO cells to produce a stable CHO cell expressing line; and, e) evaluating the cells for production of the exogenous polypeptide. In a specific embodiment, the electroporation device is a flow electroporation device. In such embodiments concerning methods for screening for high producing CHO cell lines, a further step may be employed comprising identifying a CHO cell line that is a high producer of the exogenous polypeptide.

There are also disclosed certain methods for producing a protein comprising steps of any of the methods described above and including a step of isolating or purifying an exogenous polypeptide. In certain embodiments methods also involve pooling isolated or purified exogenous polypeptides.

Also disclosed are compositions of a purified or substantially purified protein. A purified protein refers to a preparation in which the protein is the most predominant protein in the preparation. A "substantially purified protein" refers to a composition is greater than 80% pure (w/w) relative to nucleic acids and other proteins.

Such proteins may be produced by a method comprising: a) transfecting into cells an expression construct comprising a sequence i) encoding a polypeptide conferring antibiotic resistance and ii) encoding one or more exogenous polypeptide using an electroporation device; b) selecting transfected cells in media comprising a conditionally lethal concentration of antibiotic; c) isolating selected transfected cells by limiting dilution to obtain clonal cells; d) expanding isolated transfected cells to produce a stable cell expressing line; and e) collecting the exogenous polypeptide. In a specific embodiment, the electroporation device is a flow electroporation device.

As used herein the specification, "a" or "an" may mean one or more. As used herein in the claim(s), when used in conjunction with the word "comprising", the words "a" or "an" may mean one or more than one.

The use of the term "or" in the claims is used to mean "and/or" unless explicitly indicated to refer to alternatives only or the alternatives are mutually exclusive, although the disclosure supports a definition that refers to only alternatives and "and/or." As used herein "another" may mean at least a second or more.

Throughout this application, the term "about" is used to indicate that a value includes the inherent variation of error for the device, the method being employed to determine the value, or the variation that exists among the study subjects.

Other objects, features and advantages of the present invention will become apparent from the following detailed description. It should be understood, however, that the detailed description and the specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

FIG. 9: Illustrative electroporated sample conditions and results (NS: not selected)

DESCRIPTION OF ILLUSTRATIVE EMBODIMENTS

I. Stable Cell Line Development

Stable cell line development is a long and challenging process. Time, labor and cost restraints to create stable cell lines are major obstacles to advance the development of protein therapeutics. One of the key steps of stable cell line development is the transfection efficiency of CHO cells since CHO cell line is a difficult to transfect cell line. This difficulty creates the first major bottleneck to generate potential high-expressing stable cell line. However, MaxCyte STX electroporation (EP) transfection technology has shown great transfection efficiency for many difficult to transfect cell lines such as CHO cells, Jurkat cell lines, stem cells and primary cell lines (>90% efficiency). In addition, all these transfected cells have high cell viability (>90%) post EP which provides very healthy transfected cells for the stable selection. These unique transfection features of MaxCyte transfection technology allow the selection process as a very high stringent selection manner (1.6 g/L G418) to rapidly eliminate un-transfected and low expressing stable cells, increase the success rate of the stable cell line development and generate a high expressing stable cell line. The embodiments of the present invention demonstrate that a high-yield stable cell line with more than 3 g/L titer can be identified in 4-6 weeks and a fed-batch production can be done in 8 to 9 weeks by using MaxCyte transfection technology.

Figure 1:
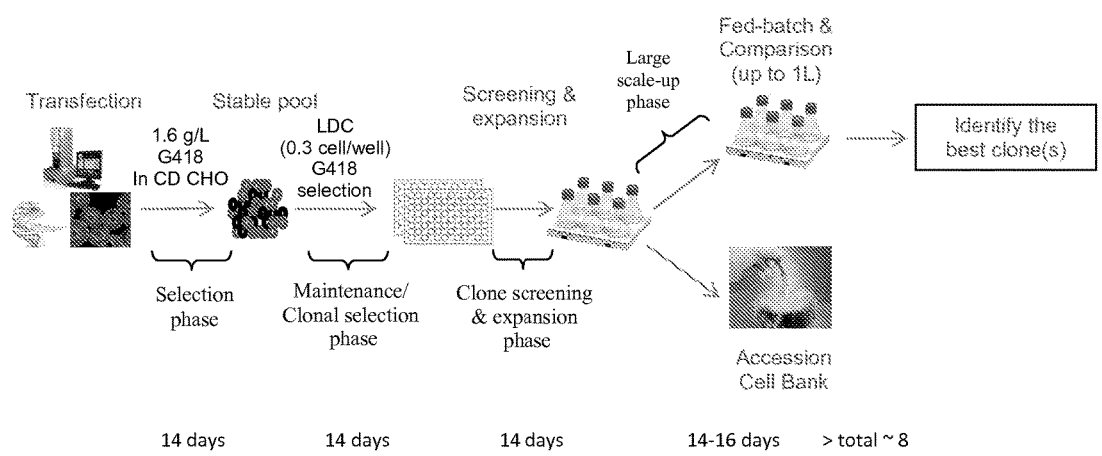
FIG. 1: The stable cell line development process with Maxcyte STX static and flow electroporation transfection technology. Figure depicts work flow of stable cell generation. After electroporation, cells may be cultured for some period of time without selection to allow for recovery from the electroporation procedure (not depicted in figure). After electroporation, cells are selected for by culturing cells in the presence of a selection agent (selection phase). After the selection phase, cells are cultured at lower density in the presence of selection agent to enable limiting dilution cloning (maintenance/clonal selection phase). After the generation of clonal populations, clones are screened for exogenous polypeptide expression and expanded (clonal screening and expansion phase). After screening, clones with desired activity are grown on larger scale for production purposes (large scale-up phase) or submitted to long-term storage such as cryopreservation.

In some embodiments, after electroporation, cells may be cultured for some period of time without selection to allow for recovery from the electroporation procedure (not depicted in figure). In other embodiments, after electroporation with recovery, cells are selected for by culturing cells in the presence of a selection agent (selection phase). In yet other embodiments, after electroporation without recovery, cells are selected for by culturing cells in the presence of a selection agent (selection phase). After the selection phase, cells are cultured at lower density in the presence of selection agent to enable limiting dilution cloning (maintenance/clonal selection phase). After the generation of clonal populations, clones are screened for exogenous polypeptide expression and expanded (clonal screening and expansion phase). After screening, clones with desired activity are grown on larger scale for production purposes (large scale-up phase) or submitted to long-term storage such as cryopreservation (FIG. 1).

In one embodiment of the methods, cells and DNA are suspended in electroporation buffer, transferred to an electroporation chamber, and subjected to a series of electrical pulses. Post electroporation, cells are transferred to culture media and cultured overnight (recovery phase). The following day 1.6 g/L G418 is added to the cultures, and cells are cultured for 14 days to kill off cells in which the plasmid DNA has not integrated (selection phase). After 14 days, cells are transferred to 96 well plates at a calculated density of 0.3 cells per well and cultured for an additional 14 days in the presence of lower G418 concentrations (maintenance/clonal section phase). After 14 days, conditioned media from individual wells are screened by immunoassay to identify clones producing high antibody titers (clone screening & expansion phase). Resulting clones are expanded in shake flasks to confirm productivity (large scale-up phase) and to generate cells for banking via cryopreservation. (FIG. 1)

II. Electroporation

Electroporation

Certain embodiments involve the use of electroporation to facilitate the entry of one or more nucleic acid molecules into host cells.

As used herein, "electroporation" or "electroloading" refers to application of an electrical current or electrical field to a cell to facilitate entry of a nucleic acid molecule into the cell. One of skill in the art would understand that any method and technique of electroporation is contemplated by the present invention.

In certain embodiments of the invention, electroloading may be carried out as described in U.S. Pat. No. 5,612,207 (specifically incorporated herein by reference), U.S. Pat. No. 5,720,921 (specifically incorporated herein by reference), U.S. Pat. No. 6,074,605 (specifically incorporated herein by reference); U.S. Pat. No. 6,090,617 (specifically incorporated herein by reference); U.S. Pat. No. 6,485,961 (specifically incorporated herein by reference); U.S. Pat. No. 7,029,916 (specifically incorporated herein by reference), U.S. Pat. No. 7,141,425 (specifically incorporated herein by reference), U.S. Pat. No. 7,186,559 (specifically incorporated herein by reference), U.S. Pat. No. 7,771,984 (specifically incorporated herein by reference), and U.S. publication number 2011/0065171 (specifically incorporated herein by reference).

Other methods and devices for electroloading that may be used in the context of the present invention are also described in, for example, published PCT Application Nos. WO 03/018751 and WO 2004/031353; U.S. patent application Ser. Nos. 10/781,440, 10/080,272, and 10/675,592; and U.S. Pat. Nos. 6,773,669, 6,090,617, 6,617,154, all of which are incorporated by reference.

In certain embodiments of the invention, electroporation may be carried out as described in U.S. patent application Ser. No. 10/225,446, filed Aug. 21, 2002, the entire disclosure of which is specifically incorporated herein by reference.

In further embodiments of the invention, flow electroporation is performed using MaxCyte STX®, MaxCyte VLX®, or MaxCyte GT® flow electroporation instrumentation.

The claimed methods of transfecting cells by electroporation, preferably flow electroporation, is capable of achieving transfection efficiencies of greater than 40%, greater than 50% and greater than 60%, 70%, 80% or 90% (or any range derivable therein). Transfection efficiency can be measured either by the percentage of the cells that express the product of the gene or the secretion level of the product express by the gene. The cells maintain a high viability during and after the electroporation process. Viability is routinely more than 50% or greater. Viability or electroporated cells can be at most or at least about 5%, 10%, 15%, 20%, 25%, 30%, 35%, 40%, 45%, 50%, 55%, 60%, 65%, 70%, 75%, 80%, 85%, 90% or 95% (or any range derivable therein). of the viability of the starting, unelectroporated population or an electroporated population transfected with a control construct.

In some embodiments the current methods use a flow electroporation apparatus for electrical stimulation of suspensions of particles, comprising a flow electroporation cell assembly having one or more inlet flow portals, one or more outlet flow portals, and one or more flow channels, the flow channels being comprised of two or more walls, with the flow channels further being configured to receive and transiently contain a continuous flow of particles in suspension from the inlet flow portals; and paired electrodes disposed in relation to the flow channels such that each electrode forms at least one wall of the flow channels, the electrodes further comprising placing the electrodes in electrical communication with a source of electrical energy, whereby suspensions of particles flowing through the channels may be subjected to an electrical field formed between the electrodes.

In some embodiments the current methods use flow electroporation to overcome the limitation of sample size. With this method, a cell suspension is passed across parallel bar electrodes that are contained in a flow cell that is preferably disposable. It is to be understood that different configurations of flow cells can be used in the current methods. During this passage, the cells are subjected to electrical pulses with predetermined characteristics. For example, the specific settings for preparation of sample cells are: voltage, 750V; pulse width, 650 μsec; time between pulses, 100 μsec; 2 biphasic pulses in a burst; time between bursts, 12 sec; flow rate, 0.05 mL/sec. The molecule or molecules of interest can then diffuse into the cell following concentration and/or electrical gradients. The present invention is optionally capable of subjecting the cells to a range of electric field strengths.

Another advantage of the current flow electroporation methods is the speed at which a large population of cells can be transfected. For example, a population of lymphocytes can be transfected by electroporation by electroporating the sample in less than 5 hours, preferably less than 4 hours and most preferable in less than 3 hours and most preferably in less than 2 hours. The time of electroporation is the time that the sample is processed by the flow electroporation process. In certain embodiments, 1E10 cells are transfected in 30 minutes or less using flow electroporation. In further embodiments, 2E11 cells may be transfected in 30 minutes, or 60 minutes or less using flow electroporation.

For flow electroporation, the process is initiated by attaching the flow cell with solutions and cell suspensions in the containers with the necessary fluids and samples. Priming solution (saline) and cell suspension are introduced by providing the required commands to the electroporation system, which controls operation of the pump and pinch valves. As the cells transit the flow path between electrodes, electric pulses of the chosen voltage, duration, and frequency are applied. Product and waste fluids are collected in the designated containers.

The user inputs the desired voltage and other parameters into the flow electroporation system of the present invention. As noted above, a range of settings is optionally available. The computer communicates to the electronics in the tower to charge the capacitor bank to the desired voltage. Appropriate switches then manipulate the voltage before it is delivered to the flow path to create the electric field (the switches provide alternating pulses or bursts to minimize electrode wear brought on by prolonged exposure to the electric field). The voltage is delivered according to the duration and frequency parameters set into the flow electroporation system of the present invention by the operator. The flow electroporation system of the present invention is now described in detail.

The flow electroporation process can be initiated by, for example, placing an electroporation chamber in fluid communication with solutions and cell suspensions in containers (e.g., via tubing), which may be carried out in an aseptic or sterile environment. A cell suspension and/or other reagents may be introduced to the electroporation chamber using one or more pumps, vacuums, valves, other mechanical devices that change the air pressure or volume inside the electroporation chamber and combinations thereof, which can cause the cell suspension and/or other reagents to flow into the electroporation chamber at a desired time and at the desired rate. If a portion of the cell suspension and/or other reagents is positioned in the electroporation chamber, electric pulses of a desired voltage, duration, and/or interval are applied the cell suspension and/or other reagents. After electroporation, the processed cell suspension and/or other reagents can be removed from the electroporation chamber using one or more pumps, vacuums, valves, other electrical, mechanical, pneumatic, or microfluidic devices that change the displacement, pressure or volume inside the electroporation chamber, and combinations thereof. In certain embodiments, gravity or manual transfer may be used to move sample or processed sample into or out of an electroporation chamber. If desired, a new cell suspension and/or other reagents can be introduced into the electroporation chamber. An electroporated sample can be collected separately from a sample that has not yet been electroporated. The preceding series of events can be coordinated temporally by a computer coupled to, for example, electronic circuitry (e.g., that provides the electrical pulse), pumps, vacuums, valves, combinations thereof, and other components that effect and control the flow of a sample into and out of the electroporation chamber. As an example, the electroporation process can be implemented by a computer, including by an operator through a graphic user interface on a monitor and/or a keyboard. Examples of suitable valves include pinch valves, butterfly valves, and/or ball valves. Examples of suitable pumps include centrifugal or positive displacement pumps.

As an example, a flow electroporation device can comprise at least two electrodes separated by a spacer, where the spacer and the at least two electrodes define a chamber. In some embodiments, the electroporation chamber can further comprise a least three ports traversing the spacer, where a first port is for sample flow into the chamber, a second port is for processed sample flow out of the chamber, and a third port is for non-sample fluid flow into or out of the chamber. In some embodiments, the non-sample fluid flows out of the chamber when a sample flows into the chamber, and the non-sample fluid flows into the chamber when processed sample flows out of the chamber. As another example, a flow electroporation device can comprise an electroporation chamber having a top and bottom portion comprising at least two parallel electrodes, the chamber being formed between the two electrodes and having two chamber ports in the bottom portion of the electroporation chamber and two chamber ports in the top portion of the electroporation chamber. Such a device can further comprise at least one sample container in fluid communication with the electroporation chamber through a first chamber port in the bottom portion of the chamber, and the electroporation chamber can be in fluid communication with the sample container through a second chamber port in the top portion of the chamber, forming a first fluid path. Further, at least one product container can be in fluid communication with the electroporation chamber through third chamber port in the bottom portion of the chamber, and the electroporation chamber can be in fluid communication with the product container through a fourth chamber port in the top portion of the chamber, forming a second fluid path. In some embodiments, a single port electroporation chamber may be used. In other embodiments, various other suitable combinations of electrodes, spacers, ports, and containers can be used. The electroporation chamber can comprise an internal volume of about 1-10 mL; however, in other embodiments, the electroporation chamber can comprise a lesser internal volume (e.g., 0.75 mL, 0.5 mL, 0.25 mL, or less) or a greater internal volume (e.g., 15 mL, 20 mL, 25 mL, or greater). In some embodiments, the electroporation chamber and associated components can be disposable (e.g., Medical Grade Class VI materials), such as PVC bags, PVC tubing, connectors, silicone pump tubing, and the like.

Any number of containers (e.g., 1, 2, 3, 4, 5, 6, or more) can be in fluid communication with the electroporation chamber. The containers may be a collapsible, expandable, or fixed volume containers. For example, a first container (e.g., a sample source or sample container) can comprise a cell suspension and may or may not include a substance that will pass into cells in the cell suspension during electroporation. If the substance is not included, a second container comprising this substance can be included such that the substance can be mixed inline before entry into the electroporation chamber or in the electroporation chamber. In an additional configuration, another container may be attached, which can hold fluid that will be discarded. One ore more additional containers can be used as the processed sample or product container. The processed sample or product container will hold cells or other products produced from the electroporation process. Further, one or more additional containers can comprise various non-sample fluids or gases that can be used to separate the sample into discrete volumes or unit volumes. The non-sample fluid or gas container can be in fluid communication with the electroporation chamber through a third and/or fourth port. The non-sample fluid or gas container may be incorporated into the processed sample container or the sample container (e.g., the non-sample fluid container can comprise a portion of the processed sample container or the sample container); and thus, the non-sample fluid or gas can be transferred from the processed sample container to another container (which may include the sample container) during the processing of the sample. The non-sample fluid or gas container may be incorporated into the chamber, as long as the compression of the non-sample fluid or gas does not affect electroporation. Further aspects of the invention may include other containers that are coupled to the sample container and may supply reagents or other samples to the chamber.

In certain aspects the density of cells during electroporation is a controlled variable. The cell density of cells during electroporation may vary or be varied according to, but not limited to, cell type, desired electroporation efficiency or desired viability of resultant electroporated cells. In certain aspects the cell density is constant throughout electroporation. In other aspects cell density is varied during the electroporation process. In certain aspects cell density before electroporation may be in the range of $1 \times 10^4$ cells/mL to $(y) \times 10^4$, where y can be 2, 3, 4, 5, 6, 7, 8, 9, or 10. In other aspects the cell density before electroporation may be in the range of $1 \times 10^5$ cells/mL to $(y) \times 10^5$, where y is 2, 3, 4, 5, 6, 7, 8, 9, or 10 (or any range derivable therein). In yet other aspects the cell density before electroporation may be in the range of $1 \times 10e6$ cells/mL to $(y) \times 10^6$, where y can be 2, 3, 4, 5, 6, 7, 8, 9, or 10. In certain aspects cell density before electroporation may be in the range of $1 \times 10^7$ cells/mL to $(y) \times 10^7$, where y can be 2, 3, 4, 5, 6, 7, 8, 9, or 10 or any range derivable therein. In yet other aspects the cell density before electroporation may be in the range of $1 \times 10^7$ cells/mL to $1 \times 10^8$ cells/mL, $1 \times 10^8$ cells/mL to $1 \times 10^9$ cells/mL, $1 \times 10^9$ cells/mL to $1 \times 10^{10}$ cells/mL, $1 \times 10^{10}$ cells/mL to $1 \times 10^{11}$ cells/mL, or $1 \times 10^{11}$ cells/mL to $1 \times 10^{12}$ cells/mL. In certain aspects the cell density before electroporation may be $(y) \times 10^6$, where y can be any of 0.01, 0.02, 0.03, 0.04, 0.05, 0.06, 0.07, 0.08, 0.09, 0.1, 0.1, 0.2, 0.3, 0.4, 0.5, 0.6, 0.7, 0.8, 0.9, 1, 1, 2, 3, 4, 5, 6, 7, 8, 9, 10, 10, 20, 30, 40, 50, 60, 70, 80, 90 or 100 or any range derivable therein. In certain aspects the cell density before electroporation may be $(y) \times 10^{10}$, where y can be any of 0.01, 0.02, 0.03, 0.04, 0.05, 0.06, 0.07, 0.08, 0.09, 0.1, 0.1, 0.2, 0.3, 0.4, 0.5, 0.6, 0.7, 0.8, 0.9, 1, 1, 2, 3, 4, 5, 6, 7, 8, 9, 10, 10, 20, 30, 40, 50, 60, 70, 80, 90, 100, 200, 300, 400, 500, 600, 700, 800, 900, or 1000 (or any range derivable therein).

In certain aspects the density of cells during electroporation is a controlled variable. The cell density of cells during electroporation may vary or be varied according to, but not limited to, cell type, desired electroporation efficiency or desired viability of resultant electroporated cells. In certain aspects the cell density is constant throughout electroporation. In other aspects cell density is varied during the electroporation process. In certain aspects cell density during electroporation may be in the range of $1 \times 10^4$ cells/mL to $(y) \times 10^4$, where y can be 2, 3, 4, 5, 6, 7, 8, 9, or 10 (or any range derivable therein). In other aspects the cell density during electroporation may be in the range of $1 \times 10^5$ cells/mL to $(y) \times 10^5$, where y is 2, 3, 4, 5, 6, 7, 8, 9, or 10 (or any range derivable therein). In yet other aspects the cell density during electroporation may be in the range of $1 \times 10^6$ cells/mL to $(y) \times 10^6$, where y can be 2, 3, 4, 5, 6, 7, 8, 9, or 10 (or any range derivable therein). In certain aspects cell density during electroporation may be in the range of $1 \times 10^7$ cells/mL to $(y) \times 10^7$, where y can be 2, 3, 4, 5, 6, 7, 8, 9, or 10 (or any range derivable therein). In yet other aspects the cell density during electroporation may be in the range of $1 \times 10^7$ cells/mL to $1 \times 10^8$ cells/mL, $1 \times 10^8$ cells/mL to $1 \times 10^9$ cells/mL, $1 \times 10^9$ cells/mL to $1 \times 10^{10}$ cells/mL, $1 \times 10^{10}$ cells/mL to $1 \times 10^{11}$ cells/mL, or $1 \times 10^{11}$ cells/mL to $1 \times 10^{12}$ cells/mL. In certain aspects the cell density during electroporation may be $(y) \times 10^6$, where y can be any of 0.01, 0.02, 0.03, 0.04, 0.05, 0.06, 0.07, 0.08, 0.09, 0.1, 0.1, 0.2, 0.3, 0.4, 0.5, 0.6, 0.7, 0.8, 0.9, 1, 1, 2, 3, 4, 5, 6, 7, 8, 9, 10, 10, 20, 30, 40, 50, 60, 70, 80, 90 or 100 (or any range derivable therein). In certain aspects the cell density during electroporation may be $(y) \times 10^{10}$, where y can be any of 0.01, 0.02, 0.03, 0.04, 0.05, 0.06, 0.07, 0.08, 0.09, 0.1, 0.1, 0.2, 0.3, 0.4, 0.5, 0.6, 0.7, 0.8, 0.9, 1, 1, 2, 3, 4, 5, 6, 7, 8, 9, 10, 10, 20, 30, 40, 50, 60, 70, 80, 90, 100, 200, 300, 400, 500, 600, 700, 800, 900, or 1000 (or any range derivable therein).

In certain aspects cell density after electroporation may be in the range of $1 \times 10^4$ cells/mL to $(y) \times 10^4$, where y can be 2, 3, 4, 5, 6, 7, 8, 9, or 10 (or any range derivable therein). In other aspects the cell density after electroporation may be in the range of $1 \times 10^5$ cells/mL to $(y) \times 10^5$, where y is 2, 3, 4, 5, 6, 7, 8, 9, or 10 (or any range derivable therein). In yet other aspects the cell density after electroporation may be in the range of $1 \times 10^6$ cells/mL to $(y) \times 10^6$, where y can be 2, 3, 4, 5, 6, 7, 8, 9, or 10 (or any range derivable therein). In certain aspects cell density after electroporation may be in the range of $1 \times 10^7$ cells/mL to $(y) \times 10^7$, where y can be 2, 3, 4, 5, 6, 7, 8, 9, or 10 (or any range derivable therein). In yet other aspects the cell density after electroporation may be in the range of $1 \times 10^7$ cells/mL to $1 \times 10^8$ cells/mL, $1 \times 10^8$ cells/mL to $1 \times 10^9$ cells/mL, $1 \times 10^9$ cells/mL to $1 \times 10^{10}$ cells/mL, $1 \times 10^{10}$ cells/mL to $1 \times 10^{11}$ cells/mL, or $1 \times 10^{11}$ cells/mL to $1 \times 10^{12}$ cells/mL (or any range derivable therein). In certain aspects the cell density after electroporation may be $(y) \times 10e6$, where y can be any of 0.01, 0.02, 0.03, 0.04, 0.05, 0.06, 0.07, 0.08, 0.09, 0.1, 0.1, 0.2, 0.3, 0.4, 0.5, 0.6, 0.7, 0.8, 0.9, 1, 1, 2, 3, 4, 5, 6, 7, 8, 9, 10, 10, 20, 30, 40, 50, 60, 70, 80, 90 or 100 (or any range derivable therein). In certain aspects the cell density after electroporation may be $(y) \times 10^{10}$, where y can be any of 0.01, 0.02, 0.03, 0.04, 0.05, 0.06, 0.07, 0.08, 0.09, 0.1, 0.1, 0.2, 0.3, 0.4, 0.5, 0.6, 0.7, 0.8, 0.9, 1, 1, 2, 3, 4, 5, 6, 7, 8, 9, 10, 10, 20, 30, 40, 50, 60, 70, 80, 90, 100, 200, 300, 400, 500, 600, 700, 800, 900, or 1000 (or any range derivable therein).

In certain embodiments electroporation can be carried out on any prokaryotic or eukaryotic cell. In some aspects electroporation involves electroporation of a human cell. In other aspects electroporation involves electroporation of an animal cell. In certain aspects electroporation involves electroporation of a cell line or a hybrid cell type. In some aspects the cell or cells being electroporated are cancer cells, tumor cells or immortalized cells. In some instances tumor, cancer, immortalized cells or cell lines are induced and in other instances tumor, cancer, immortalized cells or cell lines enter their respective state or condition naturally. In certain aspects the cells or cell lines electroporated can be A549, B-cells, B16, BHK-21, C2C12, C6, CaCo-2, CAP/, CAP-T, CHO, CHO2, CHO-DG44, CHO-K1, CHO-DUXB11 COS-1, Cos-7, CV-1, Dendritic cells, DLD-1, Embryonic Stem (ES) Cell or derivative, H1299, HEK, 293, 293T, 293FT, Hep G2, Hematopoietic Stem Cells, HOS, Huh-7, Induced Pluripotent Stem (iPS) Cell or derivative, Jurkat, K562, L5278Y, LNCaP, MCF7, MDA-MB-231, MDCK, Mesenchymal Cells, Min-6, Monocytic cell, Neuro2a, NIH 3T3, NIH3T3L1, NK-cells, NSO, Panc-1, PC12, PC-3, Peripheral blood cells, Plasma cells, Primary Fibroblasts, RBL, Renca, RLE, SF21, SF9, SH-SY5Y, SK-MES-1, SK-N-SH, SL3, SW403, Stimulus-triggered Acquisition of Pluripotency (STAP) cell or derivate SW403, T-cells, THP-1, Tumor cells, U205, U937, or Vero cells.

In certain embodiments, the cell is one that is known in the art to be difficult to transfect. Such cells are known in the art and include, for example, primary cells, insect cells, SF9 cells, Jurkat cells, CHO cells, stem cells, slowly dividing cells, and non-dividing cells.

In some instances certain number of cells can be electroporated in a certain amount of time. Given the flexibility, consistency and reproducibility of the described platform up to or more than about $(y) \times 10^4$, $(y) \times 10^5$, $(y) \times 10^6$, $(y) \times 10^7$, $(y) \times 10^8$, $(y) \times 10^9$, $(y) \times 10^{10}$, $(y) \times 10^{11}$, $(y) \times 10^{12}$, $(y) \times 10^{13}$, $(y) \times 10^{14}$, or $(y) \times 10^{15}$ cells (or any range derivable therein) can be electroporated, where y can be any of 1, 2, 3, 4, 5, 6, 7, 8, or 9 (or any range derivable therein). in less than 0.01, 0.02, 0.03, 0.04, 0.05, 0.06, 0.07, 0.08, 0.09, 0.1, 0.1, 0.2, 0.3, 0.4, 0.5, 0.6, 0.7, 0.8, 0.9, 1, 1, 2, 3, 4, 5, 6, 7, 8, 9, 10, 10, 20, 30, 40, 50, 60, 70, 80, 90 or 100 seconds (or any range derivable therein). In other instances, up to or more than about $(y) \times 10^4$, $(y) \times 10^5$, $(y) \times 10^6$, $(y) \times 10^7$, $(y) \times 10^8$, $(y) \times 10^9$, $(y) \times 10^{10}$, $(y) \times 10^{11}$, $(y) \times 10^{12}$, $(y) \times 10^{13}$, $(y) \times 10^{14}$, or $(y) \times 10^{15}$ cells (or any range derivable therein) can be electroporated, where y can be any of 1, 2, 3, 4, 5, 6, 7, 8, or 9 (or any range derivable therein), in less than 0.01, 0.02, 0.03, 0.04, 0.05, 0.06, 0.07, 0.08, 0.09, 0.1, 0.1, 0.2, 0.3, 0.4, 0.5, 0.6, 0.7, 0.8, 0.9, 1, 1, 2, 3, 4, 5, 6, 7, 8, 9, 10, 10, 20, 30, 40, 50, 60, 70, 80, 90, 100. 110, or 120 minutes (or any range derivable therein). In yet other aspects, up to or more than about $(y) \times 10^4$, $(y) \times 10^5$, $(y) \times 10^6$, $(y) \times 10^7$, $(y) \times 10^8$, $(y) \times 10^9$, $(y) \times 10^{10}$, $(y) \times 10^{11}$, $(y) \times 10^{12}$, $(y) \times 10^{13}$, $(y) \times 10^{14}$, or $(y) \times 10^{15}$ cells (or any range derivable therein) can be electroporated, where y can be any of 1, 2, 3, 4, 5, 6, 7, 8, or 9 (or any range derivable therein). in less than 1, 2, 3, 4, 5, 6, 7, 8, 9, 10, 11, 12, 13, 14, 15, 16, 17, 18, 19, 20, 21, 22, 23, or 24 hours (or any range derivable therein).

The expression '$(y) \times 10^e$' is understood to mean, a variable 'y' that can take on any numerical value, multiplied by 10 that is raised to an exponent value, e. For example, $(y) \times 10^4$, where y is 2, is understood to mean $2 \times 10^4$, which is equivalent to $2 \times 10,000$, equal to 20,000. $(y) \times 10e4$ can also be written as $(y)*10e4$ or $(y) \times 10^4$ or $(y)*10^4$.

Volumes of cells or media may vary depending on the amount of cells to be electroporated, the number of cells to be screened, the type of cells to be screened, the type of protein to be produced, amount of protein desired, cell viability, and certain cell characteristics related to desirable cell concentrations. Examples of volumes that can be used in methods and compositions include, but are not limited to, 0.1, 0.2, 0.3, 0.4, 0.5, 0.6, 0.7, 0.8, 0.9, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 110, 120, 130, 140, 150, 160, 170, 180, 190, 200, 210, 220, 230, 240, 250, 260, 270, 280, 290, 300, 310, 320, 330, 340, 350, 360, 370, 380, 390, 400, 410, 420, 430, 440, 441, 450, 460, 470, 480, 490, 500, 510, 520, 530, 540, 550, 560, 570, 580, 590, 600, 610, 620, 630, 640, 650, 660, 670, 680, 690, 700, 710, 720, 730, 740, 750, 760, 770, 780, 790, 800, 810, 820, 830, 840, 850, 860, 870, 880, 890, 900, 910, 920, 930, 940, 950, 960, 970, 980, 990, 1000 ml or L (or any range derivable therein), and any range derivable therein. Containers that may hold such volumes are contemplated for use in embodiments described herein. Such containers include, but are not limited to, cell culture dishes, petri dishes, flasks, biobags, biocontainers, bioreactors, or vats. Containers for large scale volumes are particularly contemplated, such as those capable of holding greater than 10 L or more. In certain embodiments, volumes of 100 L or more are used.

III. Cell Culture

A. Host Cells

As used herein, the terms "cell," "cell line," and "cell culture" may be used interchangeably. All of these terms also include both freshly isolated cells and ex vivo cultured, activated or expanded cells. All of these terms also include their progeny, which is any and all subsequent generations. It is understood that all progeny may not be identical due to deliberate or inadvertent mutations. In the context of expressing a heterologous nucleic acid sequence, "host cell" refers to a prokaryotic or eukaryotic cell, and it includes any transformable organism that is capable of replicating a vector or expressing a heterologous gene encoded by a vector. A host cell can, and has been, used as a recipient for vectors or viruses. A host cell may be "transfected" or "transformed," which refers to a process by which exogenous nucleic acid, such as a recombinant protein-encoding sequence, is transferred or introduced into the host cell. A transformed cell includes the primary subject cell and its progeny.

In certain embodiments cell culture after electroporation can be carried out on any prokaryotic or eukaryotic cell. In some aspects cell culture involves cell culture of a human cell. In other aspects cell culture involves cell culture of an animal cell. In certain aspects cell culture involves cell culture of a cell line or a hybrid cell type. In some aspects the cell or cells being cultured are cancer cells, tumor cells or immortalized cells. In some instances tumor, cancer, immortalized cells or cell lines are induced and in other instances tumor, cancer, immortalized cells or cell lines enter their respective state or condition naturally. In certain aspects the cells or cell lines cultured can be A549, B-cells, B16, BHK-21, C2C12, C6, CaCo-2, CAP, CAP-T, CHO, CHO2, CHO-DG44, CHO-K1, COS-1, Cos-7, CV-1, Dendritic cells, DLD-1, Embryonic Stem (ES) Cell or derivative, H1299, HEK, 293, 293T, 293FT, Hep G2, Hematopoietic Stem Cells, HOS, Huh-7, Induced Pluripotent Stem (iPS) Cell or derivative, Jurkat, K562, L5278Y, LNCaP, MCF7, MDA-MB-231, MDCK, Mesenchymal Cells, Min-6, Monocytic cell, Neuro2a, NIH 3T3, NIH3T3L1, NK-cells, NSO, Panc-1, PC12, PC-3, Peripheral blood cells, Plasma cells, Primary Fibroblasts, RBL, Renca, RLE, SF21, SF9, SH-SY5Y, SK-MES-1, SK-N-SH, SL3, SW403, Stimulus-triggered Acquisition of Pluripotency (STAP) cell or derivate SW403, T-cells, THP-1, Tumor cells, U2OS, U937, or Vero cells.

B. Selectable Agents

In certain aspects, after electroporation cells that have internalized the electroporated constructs are selected for by negative selection. In other aspects, after electroporation cells that have internalized the electroporated constructs are selected for by positive selection. In some aspects selection involves exposing the cells to concentrations of a selection agent that would compromise the viability of a cell that did not express a selection resistance gene or take up a selection resistance gene during electroporation. In some aspects selection involves exposing the cells to a conditionally lethal concentration of the selection agent. In certain aspects the selection agent or compound is an antibiotic. In other aspects the selection agent is G418 (also known as geneticin and G418 sulfate), puromycin, zeocin, hygromycin, phleomycin or blasticidin, either alone or in combination. In certain aspects the conditionally lethal concentration of selection agent is in the range of 0.1 μg/L to 0.5 μg/L, 0.5 μg/L to 1 μg/L, 1 μg/L to 2 μg/L, 2 μg/L to 5 μg/L, 5 μg/L to 10 μg/L, 10 μg/L to 100 μg/L, 100 μg/L to 500 μg/L, 0.1 mg/L to 0.5 mg/L, 0.5 mg/L to 1 mg/L, 1 mg/L to 2 mg/L, 2 mg/L to 5 mg/L, 5 mg/L to 10 mg/L, 10 mg/L to 100 mg/L, 100 mg/L to 500 mg/L, 0.1 g/L to 0.5 g/L, 0.5 g/L to 1 g/L, 1 g/L to 2 g/L, 2 g/L to 5 g/L, 5 g/L to 10 g/L, 10 g/L to 100 g/L, or 100 g/L to 500 g/L (or any range derivable therein). In certain aspects the conditionally lethal concentration of selection agent is (y)g/L, where 'y' can be any value including but not limited to 0.01, 0.02, 0.03, 0.04, 0.05, 0.06, 0.07, 0.08, 0.09, 0.1, 0.2, 0.3, 0.4, 0.5, 0.6, 0.7, 0.8, 0.9, 1, 2, 3, 4, 5, 6, 7, 8, 9, 10, 20, 30, 40, 50, 60, 70, 80, 90, 100 (or any range derivable therein). In some embodiments the selection agent is present in the culture media at a conditionally lethal concentration of about 0.1, 0.2, 0.3, 0.4, 0.5, 0.6, 0.7, 0.8, 0.9, 1, 1.1, 1.2, 1.3, 1.4, 1.5, 1.6, 1.7, 1.8, 1.9, 2, 2.1, 2.2, 2.3, 2.4, 2.5, 2.6, 2.7, 2.8, 2.9, 3, 3.1, 3.2, 3.3, 3.4, 3.5, 3.6, 3.7, 3.8, 3.9, 4, 4.1, 4.2, 4.3, 4.4, 4.5, 4.6, 4.7, 4.8, 4.9, 5, 5.1, 5.2, 5.3, 5.4, 5.5, 5.6, 5.7, 5.8, 5.9, 6, 6.1, 6.2, 6.3, 6.4, 6.5, 6.6, 6.7, 6.8, 6.9, 7, 7.1, 7.2, 7.3, 7.4, 7.5, 7.6, 7.7, 7.8, 7.9, 8, 8.1, 8.2, 8.3, 8.4, 8.5, 8.6, 8.7, 8.8, 8.9, 9, 9.1, 9.2, 9.3, 9.4, 9.5, 9.6, 9.7, 9.8, 9.9, or 10 g/L (or any range derivable therein). In certain aspects the concentration of G418 is in the range of about 0.1 μg/L to 0.5 μg/L, 0.5 μg/L to 1 μg/L, 1 μg/L to 2 μg/L, 2 μg/L to 5 μg/L, 5 μg/L to 10 μg/L, 10 μg/L to 100 μg/L, 100 μg/L to 500 μg/L, 0.1 mg/L to 0.5 mg/L, 0.5 mg/L to 1 mg/L, 1 mg/L to 2 mg/L, 2 mg/L to 5 mg/L, 5 mg/L to 10 mg/L, 10 mg/L to 100 mg/L, 100 mg/L to 500 mg/L, 0.1 g/L to 0.5 g/L, 0.5 g/L to 1 g/L, 1 g/L to 2 g/L, 2 g/L to 5 g/L, 5 g/L to 10 g/L, 10 g/L to 100 g/L, or 100 g/L to 500 g/L (or any range derivable therein). In certain aspects the concentration of G418 is (y)g/L, where 'y' can be any value including but not limited to 0.01, 0.02, 0.03, 0.04, 0.05, 0.06, 0.07, 0.08, 0.09, 0.1, 0.2, 0.3, 0.4, 0.5, 0.6, 0.7, 0.8, 0.9, 1, 2, 3, 4, 5, 6, 7, 8, 9, 10, 20, 30, 40, 50, 60, 70, 80, 90, 100 (or any range derivable therein). In some embodiments the G418 is present in the culture media at a concentration of about 0.1, 0.2, 0.3, 0.4, 0.5, 0.6, 0.7, 0.8, 0.9, 1, 1.1, 1.2, 1.3, 1.4, 1.5, 1.6, 1.7, 1.8, 1.9, 2, 2.1, 2.2, 2.3, 2.4, 2.5, 2.6, 2.7, 2.8, 2.9, 3, 3.1, 3.2, 3.3, 3.4, 3.5, 3.6, 3.7, 3.8, 3.9, 4, 4.1, 4.2, 4.3, 4.4, 4.5, 4.6, 4.7, 4.8, 4.9, 5, 5.1, 5.2, 5.3, 5.4, 5.5, 5.6, 5.7, 5.8, 5.9, 6, 6.1, 6.2, 6.3, 6.4, 6.5, 6.6, 6.7, 6.8, 6.9, 7, 7.1, 7.2, 7.3, 7.4, 7.5, 7.6, 7.7, 7.8, 7.9, 8, 8.1, 8.2, 8.3, 8.4, 8.5, 8.6, 8.7, 8.8, 8.9, 9, 9.1, 9.2, 9.3, 9.4, 9.5, 9.6, 9.7, 9.8, 9.9, or 10 g/L (or any range derivable therein).

In certain aspects, the selection agent is G418 and is present at a conditionally lethal concentration. In some embodiments, the conditionally lethal concentration is at least 0.3, 0.4, 0.5, 0.6, 0.7, 0.8, 0.9, 1, 1.1, 1.2, 1.3, 1.4, 1.5, 1.6, 1.7, 1.8, 1.9, 2, 2.1, 2.2, 2.3, 2.4, 2.5, 2.6, 2.7, 2.8, 2.9, 3, 3.1, or 3.2 mg/mL. In further embodiments, the conditionally lethal concentration of G418 is at most 1.4, 1.5, 1.6, 1.7, 1.8, 1.9, 2, 2.1, 2.2, 2.3, 2.4, 2.5, 2.6, 2.7, 2.8, 2.9, 3, 3.1, 3.2, 3.3, 3.4, 3.5, 3.6, 3.7, 3.8, 3.9, 4, 4.1, 4.2, 4.3, 4.4, 4.5, 4.6, 4.7, 4.8, 4.9, 5, 5.1, 5.2, 5.3, 5.4, 5.5, 5.6, 5.7 mg/mL. In further embodiments, the conditionally lethal concentration of G418 is from 1 mg/mL to 1.5 mg/mL, from 1 mg/mL to 1.75 mg/mL, from 1 mg/mL to 2 mg/mL, from 1 mg/mL to 2.25 mg/mL, from 1 mg/mL to 2.5 mg/mL, from 1 mg/mL to 2.75 mg/mL, from 1 mg/mL to 3 mg/mL, from 1 mg/mL to 3.25 mg/mL, from 1 mg/mL to 3.5 mg/mL, from 1 mg/mL to 4 mg/mL, from 1 mg/mL to 4.5 mg/mL, from 1 mg/mL to 5 mg/mL, from 1 mg/mL to 5.5 mg/mL, from 1.25 mg/mL to 1.5 mg/mL, from 1.25 mg/mL to 1.75 mg/mL, from 1.25 mg/mL to 2 mg/mL, from 1.25 mg/mL to 2.25 mg/mL, from 1.25 mg/mL to 2.5 mg/mL, from 1.25 mg/mL to 2.75 mg/mL, from 1.25 mg/mL to 3 mg/mL, from 1.25 mg/mL to 3.25 mg/mL, from 1.25 mg/mL to 3.5 mg/mL, from 1.25 mg/mL to 4 mg/mL, from 1.25 mg/mL to 4.5 mg/mL, from 1.25 mg/mL to 5 mg/mL, from 1.25 mg/mL to 5.5 mg/mL, from 1.5 mg/mL to 1.75 mg/mL, from 1.5 mg/mL to 2 mg/mL, from 1.5 mg/mL to 2.25 mg/mL, from 1.5 mg/mL to 2.5 mg/mL, from 1.5 mg/mL to 2.75 mg/mL, from 1.5 mg/mL to 3 mg/mL, from 1.5 mg/mL to 3.25 mg/mL, from 1.5 mg/mL to 3.5 mg/mL, from 1.5 mg/mL to 4 mg/mL, from 1.5 mg/mL to 4.5 mg/mL, from 1.5 mg/mL to 5 mg/mL, from 1.5 mg/mL to 5.5 mg/mL, from 1.75 mg/mL to 2 mg/mL, from 1.75 mg/mL to 2.25 mg/mL, from 1.75 mg/mL to 2.5 mg/mL, from 1.75 mg/mL to 2.75 mg/mL, from 1.75 mg/mL to 3 mg/mL, from 1.75 mg/mL to 3.25 mg/mL, from 1.75 mg/mL to 3.5 mg/mL, from 1.75 mg/mL to 4 mg/mL, from 1.75 mg/mL to 4.5 mg/mL, from 1.75 mg/mL to 5 mg/mL, from 1.75 mg/mL to 5.5 mg/mL, 2 mg/mL to 2.25 mg/mL, from 2 mg/mL to 2.5 mg/mL, from 2 mg/mL to 2.75 mg/mL, from 2 mg/mL to 3 mg/mL, from 2 mg/mL to 3.25 mg/mL, from 2 mg/mL to 3.5 mg/mL, from 2 mg/mL to 4 mg/mL, from 2 mg/mL to 4.5 mg/mL, from 2 mg/mL to 5 mg/mL, from 2 mg/mL to 5.5 mg/mL, from 2.25 mg/mL to 2.5 mg/mL, from 2.25 mg/mL to 2.75 mg/mL, from 2.25 mg/mL to 3 mg/mL, from 2.25 mg/mL to 3.25 mg/mL, from 2.25 mg/mL to 3.5 mg/mL, from 2.25 mg/mL to 4 mg/mL, from 2.25 mg/mL to 4.5 mg/mL, from 2.25 mg/mL to 5 mg/mL, from 2.25 mg/mL to 5.5 mg/mL, from 2.5 mg/mL to 2.75 mg/mL, from 2.5 mg/mL to 3 mg/mL, from 2.5 mg/mL to 3.25 mg/mL, from 2.5 mg/mL to 3.5 mg/mL, from 2.5 mg/mL to 4 mg/mL, from 2.5 mg/mL to 4.5 mg/mL, from 2.5 mg/mL to 5 mg/mL, from 2.5 mg/mL to 5.5 mg/mL, from 2.75 mg/mL to 3 mg/mL, from 2.75 mg/mL to 3.25 mg/mL, from 2.75 mg/mL to 3.5 mg/mL, from 2.75 mg/mL to 4 mg/mL, from 2.75 mg/mL to 4.5 mg/mL, from 2.75 mg/mL to 5 mg/mL, or from 2.75 mg/mL to 5.5 mg/mL.

In certain aspects, the selection agent is hygromycin and is present at a conditionally lethal concentration. In some embodiments, the conditionally lethal concentration is at least 0.3, 0.4, 0.5, 0.6, 0.7, 0.8, 0.9, 1, 1.1, 1.2, 1.3, 1.4, 1.5, 1.6, 1.7, 1.8, 1.9, 2, 2.1, 2.2, 2.3, 2.4, 2.5, 2.6, 2.7, 2.8, 2.9, 3, 3.1, or 3.2 mg/mL. In further embodiments, the conditionally lethal concentration of hygromycin is at most 1.4, 1.5, 1.6, 1.7, 1.8, 1.9, 2, 2.1, 2.2, 2.3, 2.4, 2.5, 2.6, 2.7, 2.8, 2.9, 3, 3.1, 3.2, 3.3, 3.4, 3.5, 3.6, 3.7, 3.8, 3.9, 4, 4.1, 4.2, 4.3, 4.4, 4.5, 4.6, 4.7, 4.8, 4.9, 5, 5.1, 5.2, 5.3, 5.4, 5.5, 5.6, 5.7 mg/mL. In further embodiments, the conditionally lethal concentration of hygromycin is from 1 mg/mL to 1.5 mg/mL, from 1 mg/mL to 1.75 mg/mL, from 1 mg/mL to 2 mg/mL, from 1 mg/mL to 2.25 mg/mL, from 1 mg/mL to 2.5 mg/mL, from 1 mg/mL to 2.75 mg/mL, from 1 mg/mL to 3 mg/mL, from 1 mg/mL to 3.25 mg/mL, from 1 mg/mL to 3.5 mg/mL, from 1 mg/mL to 4 mg/mL, from 1 mg/mL to 4.5 mg/mL, from 1 mg/mL to 5 mg/mL, from 1 mg/mL to 5.5 mg/mL, from 1.25 mg/mL to 1.5 mg/mL, from 1.25 mg/mL to 1.75 mg/mL, from 1.25 mg/mL to 2 mg/mL, from 1.25 mg/mL to 2.25 mg/mL, from 1.25 mg/mL to 2.5 mg/mL, from 1.25 mg/mL to 2.75 mg/mL, from 1.25 mg/mL to 3 mg/mL, from 1.25 mg/mL to 3.25 mg/mL, from 1.25 mg/mL to 3.5 mg/mL, from 1.25 mg/mL to 4 mg/mL, from 1.25 mg/mL to 4.5 mg/mL, from 1.25 mg/mL to 5 mg/mL, from 1.25 mg/mL to 5.5 mg/mL, from 1.5 mg/mL to 1.75 mg/mL, from 1.5 mg/mL to 2 mg/mL, from 1.5 mg/mL to 2.25 mg/mL, from 1.5 mg/mL to 2.5 mg/mL, from 1.5 mg/mL to 2.75 mg/mL, from 1.5 mg/mL to 3 mg/mL, from 1.5 mg/mL to 3.25 mg/mL, from 1.5 mg/mL to 3.5 mg/mL, from 1.5 mg/mL to 4 mg/mL, from 1.5 mg/mL to 4.5 mg/mL, from 1.5 mg/mL to 5 mg/mL, from 1.5 mg/mL to 5.5 mg/mL, from 1.75 mg/mL to 2 mg/mL, from 1.75 mg/mL to 2.25 mg/mL, from 1.75 mg/mL to 2.5 mg/mL, from 1.75 mg/mL to 2.75 mg/mL, from 1.75 mg/mL to 3 mg/mL, from 1.75 mg/mL to 3.25 mg/mL, from 1.75 mg/mL to 3.5 mg/mL, from 1.75 mg/mL to 4 mg/mL, from 1.75 mg/mL to 4.5 mg/mL, from 1.75 mg/mL to 5 mg/mL, from 1.75 mg/mL to 5.5 mg/mL, 2 mg/mL to 2.25 mg/mL, from 2 mg/mL to 2.5 mg/mL, from 2 mg/mL to 2.75 mg/mL, from 2 mg/mL to 3 mg/mL, from 2 mg/mL to 3.25 mg/mL, from 2 mg/mL to 3.5 mg/mL, from 2 mg/mL to 4 mg/mL, from 2 mg/mL to 4.5 mg/mL, from 2 mg/mL to 5 mg/mL, from 2 mg/mL to 5.5 mg/mL, from 2.25 mg/mL to 2.5 mg/mL, from 2.25 mg/mL to 2.75 mg/mL, from 2.25 mg/mL to 3 mg/mL, from 2.25 mg/mL to 3.25 mg/mL, from 2.25 mg/mL to 3.5 mg/mL, from 2.25 mg/mL to 4 mg/mL, from 2.25 mg/mL to 4.5 mg/mL, from 2.25 mg/mL to 5 mg/mL, from 2.25 mg/mL to 5.5 mg/mL, from 2.5 mg/mL to 2.75 mg/mL, from 2.5 mg/mL to 3 mg/mL, from 2.5 mg/mL to 3.25 mg/mL, from 2.5 mg/mL to 3.5 mg/mL, from 2.5 mg/mL to 4 mg/mL, from 2.5 mg/mL to 4.5 mg/mL, from 2.5 mg/mL to 5 mg/mL, from 2.5 mg/mL to 5.5 mg/mL, from 2.75 mg/mL to 3 mg/mL, from 2.75 mg/mL to 3.25 mg/mL, from 2.75 mg/mL to 3.5 mg/mL, from 2.75 mg/mL to 4 mg/mL, from 2.75 mg/mL to 4.5 mg/mL, from 2.75 mg/mL to 5 mg/mL, or from 2.75 mg/mL to 5.5 mg/mL.

In certain aspects, the selection agent is zeocin and is present at a conditionally lethal concentration. In some embodiments, the conditionally lethal concentration is at least 0.3, 0.4, 0.5, 0.6, 0.7, 0.8, 0.9, 1, 1.1, 1.2, 1.3, 1.4, 1.5, 1.6, 1.7, 1.8, 1.9, 2, 2.1, 2.2, 2.3, 2.4, 2.5, 2.6, 2.7, 2.8, 2.9, 3, 3.1, or 3.2 mg/mL. In further embodiments, the conditionally lethal concentration of zeocin is at most 1.4, 1.5, 1.6, 1.7, 1.8, 1.9, 2, 2.1, 2.2, 2.3, 2.4, 2.5, 2.6, 2.7, 2.8, 2.9, 3, 3.1, 3.2, 3.3, 3.4, 3.5, 3.6, 3.7, 3.8, 3.9, 4, 4.1, 4.2, 4.3, 4.4, 4.5, 4.6, 4.7, 4.8, 4.9, 5, 5.1, 5.2, 5.3, 5.4, 5.5, 5.6, 5.7 mg/mL. In further embodiments, the conditionally lethal concentration of zeocin is from 1 mg/mL to 1.5 mg/mL, from 1 mg/mL to 1.75 mg/mL, from 1 mg/mL to 2 mg/mL, from 1 mg/mL to 2.25 mg/mL, from 1 mg/mL to 2.5 mg/mL, from 1 mg/mL to 2.75 mg/mL, from 1 mg/mL to 3 mg/mL, from 1 mg/mL to 3.25 mg/mL, from 1 mg/mL to 3.5 mg/mL, from 1 mg/mL to 4 mg/mL, from 1 mg/mL to 4.5 mg/mL, from 1 mg/mL to 5 mg/mL, from 1 mg/mL to 5.5 mg/mL, from 1.25 mg/mL to 1.5 mg/mL, from 1.25 mg/mL to 1.75 mg/mL, from 1.25 mg/mL to 2 mg/mL, from 1.25 mg/mL to 2.25 mg/mL, from 1.25 mg/mL to 2.5 mg/mL, from 1.25 mg/mL to 2.75 mg/mL, from 1.25 mg/mL to 3 mg/mL, from 1.25 mg/mL to 3.25 mg/mL, from 1.25 mg/mL to 3.5 mg/mL, from 1.25 mg/mL to 4 mg/mL, from 1.25 mg/mL to 4.5 mg/mL, from 1.25 mg/mL to 5 mg/mL, from 1.25 mg/mL to 5.5 mg/mL, from 1.5 mg/mL to 1.75 mg/mL, from 1.5 mg/mL to 2 mg/mL, from 1.5 mg/mL to 2.25 mg/mL, from 1.5 mg/mL to 2.5 mg/mL, from 1.5 mg/mL to 2.75 mg/mL, from 1.5 mg/mL to 3 mg/mL, from 1.5 mg/mL to 3.25 mg/mL, from 1.5 mg/mL to 3.5 mg/mL, from 1.5 mg/mL to 4 mg/mL, from 1.5 mg/mL to 4.5 mg/mL, from 1.5 mg/mL to 5 mg/mL, from 1.5 mg/mL to 5.5 mg/mL, from 1.75 mg/mL to 2 mg/mL, from 1.75 mg/mL to 2.25 mg/mL, from 1.75 mg/mL to 2.5 mg/mL, from 1.75 mg/mL to 2.75 mg/mL, from 1.75 mg/mL to 3 mg/mL, from 1.75 mg/mL to 3.25 mg/mL, from 1.75 mg/mL to 3.5 mg/mL, from 1.75 mg/mL to 4 mg/mL, from 1.75 mg/mL to 4.5 mg/mL, from 1.75 mg/mL to 5 mg/mL, from 1.75 mg/mL to 5.5 mg/mL, 2 mg/mL to 2.25 mg/mL, from 2 mg/mL to 2.5 mg/mL, from 2 mg/mL to 2.75 mg/mL, from 2 mg/mL to 3 mg/mL, from 2 mg/mL to 3.25 mg/mL, from 2 mg/mL to 3.5 mg/mL, from 2 mg/mL to 4 mg/mL, from 2 mg/mL to 4.5 mg/mL, from 2 mg/mL to 5 mg/mL, from 2 mg/mL to 5.5 mg/mL, from 2.25 mg/mL to 2.5 mg/mL, from 2.25 mg/mL to 2.75 mg/mL, from 2.25 mg/mL to 3 mg/mL, from 2.25 mg/mL to 3.25 mg/mL, from 2.25 mg/mL to 3.5 mg/mL, from 2.25 mg/mL to 4 mg/mL, from 2.25 mg/mL to 4.5 mg/mL, from 2.25 mg/mL to 5 mg/mL, from 2.25 mg/mL to 5.5 mg/mL, from 2.5 mg/mL to 2.75 mg/mL, from 2.5 mg/mL to 3 mg/mL, from 2.5 mg/mL to 3.25 mg/mL, from 2.5 mg/mL to 3.5 mg/mL, from 2.5 mg/mL to 4 mg/mL, from 2.5 mg/mL to 4.5 mg/mL, from 2.5 mg/mL to 5 mg/mL, from 2.5 mg/mL to 5.5 mg/mL, from 2.75 mg/mL to 3 mg/mL, from 2.75 mg/mL to 3.25 mg/mL, from 2.75 mg/mL to 3.5 mg/mL, from 2.75 mg/mL to 4 mg/mL, from 2.75 mg/mL to 4.5 mg/mL, from 2.75 mg/mL to 5 mg/mL, or from 2.75 mg/mL to 5.5 mg/mL.

In certain aspects, the selection agent is puromycin and is present at a conditionally lethal concentration. In some embodiments, the conditionally lethal concentration is at least 3, 4, 5, 6, 7, 8, 9, 10, 11, 12, 13, 14, 15, 16, 17, 18, 19, 20, 21, 22, 23, 24, 25, 26, 27, 28, 29, 30, 35, 40, or 45 µg/mL. In further embodiments, the conditionally lethal concentration of puromycin is at most 11, 12, 13, 14, 15, 16, 17, 18, 19, 20, 21, 22, 23, 24, 25, 26, 27, 28, 29, 30, 35, 40, 45, 50, or 55 µg/mL. In further embodiments, the conditionally lethal concentration of puromycin is from 5 µg/mL to 10 µg/mL, from 5 µg/mL to 15 µg/mL, from 5 µg/mL to 20 µg/mL, from 5 µg/mL to 25 µg/mL, from 5 µg/mL to 30 µg/mL, from 5 µg/mL to 35 µg/mL, from 5 µg/mL to 40 µg/mL, from 5 µg/mL to 45 µg/mL, from 5 µg/mL to 50 µg/mL, from 5 µg/mL to 55 µg/mL, from 10 µg/mL to 15 µg/mL, from 10 µg/mL to 20 µg/mL, from 10 µg/mL to 25 µg/mL, from 10 µg/mL to 30 µg/mL, from 10 µg/mL to 35 µg/mL, from 10 µg/mL to 40 µg/mL, from 10 µg/mL to 45 µg/mL, from 10 µg/mL to 50 µg/mL, from 10 µg/mL to 55 µg/mL, from 15 µg/mL to 20 µg/mL, from 15 µg/mL to 25 µg/mL, from 15 µg/mL to 30 µg/mL, from 15 µg/mL to 35 µg/mL, from 15 µg/mL to 40 µg/mL, from 15 µg/mL to 45 µg/mL, from 15 µg/mL to 50 µg/mL, from 15 µg/mL to 55 µg/mL, from 20 µg/mL to 25 µg/mL, from 20 µg/mL to 30 µg/mL, from 20 µg/mL to 35 µg/mL, from 20 µg/mL to 40 µg/mL, from 20 µg/mL to 45 µg/mL, from 20 µg/mL to 50 µg/mL, from 20 µg/mL to 55 µg/mL, from 25 µg/mL to 30 µg/mL, from 25 µg/mL to 35 µg/mL, 25 µg/mL to 40 µg/mL, from 25 µg/mL to 45 µg/mL, from 25 µg/mL to 50 µg/mL, from 25 µg/mL to 55 µg/mL, from 30 µg/mL to 40 µg/mL, from 30 µg/mL to 50 µg/mL, from 30 µg/mL to 55 µg/mL, or from 40 µg/mL to 55 µg/mL.

In certain aspects, the selection agent is blasticidin and is present at a conditionally lethal concentration. In some embodiments, the conditionally lethal concentration is at least 10, 11, 12, 13, 14, 15, 16, 17, 18, 19, 20, 21, 22, 23, 24, 25, 26, 27, 28, 29, 30, 35, 40, 45, 50, 60, 70, 80, 90, 100, 120, 140, or 160 µg/mL. In further embodiments, the conditionally lethal concentration of blasticidin is at most 15, 20, 30, 40, 50, 60, 80, 100, 120, 140, or 160 µg/mL. In further embodiments, the conditionally lethal concentration of blasticidin is from 5 µg/mL to 10 µg/mL, from 5 µg/mL to 20 µg/mL, from 5 µg/mL to 30 µg/mL, from 5 µg/mL to 40 µg/mL, from 5 µg/mL to 50 µg/mL, from 5 µg/mL to 60 µg/mL, from 5 µg/mL to 70 µg/mL, from 5 µg/mL to 80 µg/mL, from 5 µg/mL to 90 µg/mL, from 5 µg/mL to 100 µg/mL, from 5 µg/mL to 120 µg/mL, from 5 µg/mL to 140 µg/mL, from 5 µg/mL to 160 µg/mL, from 10 µg/mL to 20 µg/mL, from 10 µg/mL to 30 µg/mL, from 10 µg/mL to 40 µg/mL, from 10 µg/mL to 50 µg/mL, from 10 µg/mL to 60 µg/mL, from 10 µg/mL to 70 µg/mL, from 10 µg/mL to 80 µg/mL, from 10 µg/mL to 90 µg/mL, from 10 µg/mL to 100 µg/mL, from 10 µg/mL to 120 µg/mL, from 10 µg/mL to 140 µg/mL, from 10 µg/mL to 160 µg/mL, from 20 µg/mL to 30 µg/mL, from 20 µg/mL to 40 µg/mL, from 20 µg/mL to 50 µg/mL, from 20 µg/mL to 60 µg/mL, from 20 µg/mL to 70 µg/mL, from 20 µg/mL to 80 µg/mL, from 20 µg/mL to 90 µg/mL, from 20 µg/mL to 100 µg/mL, from 20 µg/mL to 120 µg/mL, from 20 µg/mL to 140 µg/mL, from 20 µg/mL to 160 µg/mL, from 30 µg/mL to 40 µg/mL, from 30 µg/mL to 50 µg/mL, from 30 µg/mL to 60 µg/mL, from 30 µg/mL to 70 µg/mL, from 30 µg/mL to 80 µg/mL, from 30 µg/mL to 90 µg/mL, from 30 µg/mL to 100 µg/mL, from 30 µg/mL to 120 µg/mL, from 30 µg/mL to 140 µg/mL, from 30 µg/mL to 160 µg/mL, from 40 µg/mL to 50 µg/mL, from 40 µg/mL to 60 µg/mL, from 40 µg/mL to 70 µg/mL, from 40 µg/mL to 80 µg/mL, from 40 µg/mL to 90 µg/mL, from 40 µg/mL to 100 µg/mL, from 40 µg/mL to 120 µg/mL, from 40 µg/mL to 140 µg/mL, from 40 µg/mL to 160 µg/mL, from 50 µg/mL to 60 µg/mL, from 50 µg/mL to 70 µg/mL, from 50 µg/mL to 80 µg/mL, from 50 µg/mL to 90 µg/mL, from 50 µg/mL to 100 µg/mL, from 50 µg/mL to 120 µg/mL, from 50 µg/mL to 140 µg/mL, from 50 µg/mL to 160 µg/mL, from 60 µg/mL to 70 µg/mL, from 60 µg/mL to 80 µg/mL, from 60 µg/mL to 90 µg/mL, from 60 µg/mL to 100 µg/mL, from 60 µg/mL to 120 µg/mL, from 60 µg/mL to 140 µg/mL, from 60 µg/mL to 160 µg/mL, from 70 µg/mL to 80 µg/mL, from 70 µg/mL to 90 µg/mL, from 70 µg/mL to 100 µg/mL, from 70 µg/mL to 120 µg/mL, from 70 µg/mL to 140 µg/mL, from 70 µg/mL to 160 µg/mL, from 80 µg/mL to 90 µg/mL, from 80 µg/mL to 100 µg/mL, from 80 µg/mL to 120 µg/mL, from 80 µg/mL to 140 µg/mL, from 80 µg/mL to 160 µg/mL, from 90 µg/mL to 160 µg/mL, from 100 µg/mL to 160 µg/mL, or from 120 µg/mL to 160 µg/mL.

In certain aspects, the selection agent is phleomycin and is present at a conditionally lethal concentration. In some embodiments, the conditionally lethal concentration is at least 15, 16, 17, 18, 19, 20, 21, 22, 23, 24, 25, 26, 27, 28, 29, 30, 35, 40, 45, 50, 60, 70, 80, 90, 100, 120, 140, 160, 180, or 200 µg/mL. In further embodiments, the conditionally lethal concentration of phleomycin is at most 50, 75, 100, 125, 200, 225, 250, or 300 µg/mL. In further embodiments, the conditionally lethal concentration of phleomycin is from 15 µg/mL to 25 µg/mL, from 15 µg/mL to 75 µg/mL, from 15 µg/mL to 100 µg/mL, from 15 µg/mL to 125 µg/mL, from 15 µg/mL to 150 µg/mL, from 15 µg/mL to 175 µg/mL, from 15 µg/mL to 200 µg/mL, from 15 µg/mL to 225 µg/mL, from 15 µg/mL to 250 µg/mL, from 15 µg/mL to 300 µg/mL, from 25 µg/mL to 75 µg/mL, from 25 µg/mL to 100 µg/mL, from 25 µg/mL to 125 µg/mL, from 25 µg/mL to 150 µg/mL, from 25 µg/mL to 175 µg/mL, from 25 µg/mL to 200 µg/mL, from 25 µg/mL to 225 µg/mL, from 25 µg/mL to 250 µg/mL, from 25 µg/mL to 300 µg/mL, from 50 µg/mL to 75 µg/mL, from 50 µg/mL to 100 µg/mL, from 50 µg/mL to 125 µg/mL, from 50 µg/mL to 150 µg/mL, from 50 µg/mL to 175 µg/mL, from 50 µg/mL to 200 µg/mL, from 50 µg/mL to 225 µg/mL, from 50 µg/mL to 250 µg/mL, from 50 µg/mL to 300 µg/mL, from 60 µg/mL to 75 µg/mL, from 60 µg/mL to 100 µg/mL, from 60 µg/mL to 125 µg/mL, from 60 µg/mL to 150 µg/mL, from 60 µg/mL to 175 µg/mL, from 60 µg/mL to 200 µg/mL, from 60 µg/mL to 225 µg/mL, from 60 µg/mL to 250 µg/mL, from 60 µg/mL to 300 µg/mL, from 80 µg/mL to 100 µg/mL, from 80 µg/mL to 125 µg/mL, from 80 µg/mL to 150 µg/mL, from 80 µg/mL to 175 µg/mL, from 80 µg/mL to 200 µg/mL, from 80 µg/mL to 225 µg/mL, from 80 µg/mL to 250 µg/mL, from 80 µg/mL to 300 µg/mL, from 100 µg/mL to 125 µg/mL, from 100 µg/mL to 150 µg/mL, from 100 µg/mL to 175 µg/mL, from 100 µg/mL to 200 µg/mL, from 100 µg/mL to 225 µg/mL, from 100 µg/mL to 250 µg/mL, from 100 µg/mL to 300 µg/mL, from 120 µg/mL to 150 µg/mL, from 120 µg/mL to 175 µg/mL, from 120 µg/mL to 200 µg/mL, from 120 µg/mL to 225 µg/mL, from 120 µg/mL to 250 µg/mL, from 120 µg/mL to 300 µg/mL, from 140 µg/mL to 175 µg/mL, from 140 µg/mL to 200 µg/mL, from 140 µg/mL to 225 µg/mL, from 140 µg/mL to 250 µg/mL, from 140 µg/mL to 300 µg/mL, from 160 µg/mL to 175 µg/mL, from 160 µg/mL to 200 µg/mL, from 160 µg/mL to 225 µg/mL, from 160 µg/mL to 250 µg/mL, from 160 µg/mL to 300 µg/mL, from 180 µg/mL to 200 µg/mL, from 180 µg/mL to 225 µg/mL, from 180 µg/mL to 250 µg/mL, from 180 µg/mL to 300 µg/mL, from 200 µg/mL to 225 µg/mL, from 200 µg/mL to 250 µg/mL, from 200 µg/mL to 300 µg/mL, from 220 µg/mL to 250 µg/mL, from 220 µg/mL to 300 µg/mL, or from 240 µg/mL to 300 µg/mL.

In certain aspects, the selection agent is bleomycin and is present at a conditionally lethal concentration. In some embodiments, the conditionally lethal concentration is at least 30, 35, 40, 45, 50, 75, 100, 110, 120, 130, 140, 150, 160, 170, 180, 190, 200, 220, 230, 240, 250, 260, 270, 280, 290, 300, 310, 320, 330, 340, 350, 360, 370, 380, 390, 400, 410, 420, 430, 440, 450, 460, 470, 480, 490, 500, 525, 550, 575, 600, 625, 650, 675, 700, 800 or 900 µg/mL. In further embodiments, the conditionally lethal concentration of bleomycin is at most 125, 150, 175, 200, 225, 250, 275, 300, 325, 350, 375, 400, 425, 450, 475, 500, 525, 550, 575, 600, 625, 650, 675, 700, 800 or 900 µg/mL. In further embodiments, the conditionally lethal concentration of bleomycin is from 30 µg/mL to 125 µg/mL, from 30 µg/mL to 150 µg/mL, from 30 µg/mL to 175 µg/mL, from 30 µg/mL to 200 µg/mL, from 30 µg/mL to 225 µg/mL, from 30 µg/mL to 250 µg/mL, from 30 µg/mL to 275 µg/mL, from 30 µg/mL to 300 µg/mL, from 30 µg/mL to 325 µg/mL, from 30 µg/mL to 350 µg/mL, from 30 µg/mL to 375 µg/mL, from 30 µg/mL to 400 µg/mL, from 30 µg/mL to 425 µg/mL, from 30 µg/mL to 450 µg/mL, from 30 µg/mL to 475 µg/mL, from 30 µg/mL to 500 µg/mL, from 30 µg/mL to 600 µg/mL, from 30 µg/mL to 700 µg/mL, from 50 µg/mL to 125 µg/mL, from 50 µg/mL to 150 µg/mL, from 50 µg/mL to 175 µg/mL, from 50 µg/mL to 200 µg/mL, from 50 µg/mL to 225 µg/mL, from 50 µg/mL to 250 µg/mL, from 50 µg/mL to 275 µg/mL, from 50 µg/mL to 300 µg/mL, from 50 µg/mL to 325 µg/mL, from 50 µg/mL to 350 µg/mL, from 50 µg/mL to 375 µg/mL, from 50 µg/mL to 400 µg/mL, from 50 µg/mL to 425 µg/mL, from 50 µg/mL to 450 µg/mL, from 50 µg/mL to 475 µg/mL, from 50 µg/mL to 500 µg/mL, from 50 µg/mL to 600 µg/mL, from 50 µg/mL to 700 µg/mL, from 100 µg/mL to 125 µg/mL, from 100 µg/mL to 150 µg/mL, from 100 µg/mL to 175 µg/mL, from 100 µg/mL to 200 µg/mL, from 100 µg/mL to 225 µg/mL, from 100 µg/mL to 250 µg/mL, from 100 µg/mL to 275 µg/mL, from 100 µg/mL to 300 µg/mL, from 100 µg/mL to 325 µg/mL, from 100 µg/mL to 350 µg/mL, from 100 µg/mL to 375 µg/mL, from 100 µg/mL to 400 µg/mL, from 100 µg/mL to 425 µg/mL, from 100 µg/mL to 450 µg/mL, from 100 µg/mL to 475 µg/mL, from 100 µg/mL to 500 µg/mL, from 100 µg/mL to 600 µg/mL, from 100 µg/mL to 700 µg/mL, from 150 µg/mL to 175 µg/mL, from 150 µg/mL to 200 µg/mL, from 150 µg/mL to 225 µg/mL, from 150 µg/mL to 250 µg/mL, from 150 µg/mL to 275 µg/mL, from 150 µg/mL to 300 µg/mL, from 150 µg/mL to 325 µg/mL, from 150 µg/mL to 350 µg/mL, from 150 µg/mL to 375 µg/mL, from 150 µg/mL to 400 µg/mL, from 150 µg/mL to 425 µg/mL, from 150 µg/mL to 450 µg/mL, from 150 µg/mL to 475 µg/mL, from 150 µg/mL to 500 µg/mL, from 150 µg/mL to 600 µg/mL, from 150 µg/mL to 700 µg/mL, from 175 µg/mL to 200 µg/mL, from 175 µg/mL to 225 µg/mL, from 175 µg/mL to 250 µg/mL, from 175 µg/mL to 275 µg/mL, from 175 µg/mL to 300 µg/mL, from 175 µg/mL to 325 µg/mL, from 175 µg/mL to 350 µg/mL, from 175 µg/mL to 375 µg/mL, from 175 µg/mL to 400 µg/mL, from 175 µg/mL to 425 µg/mL, from 175 µg/mL to 450 µg/mL, from 175 µg/mL to 475 µg/mL, from 175 µg/mL to 500 µg/mL, from 175 µg/mL to 600 µg/mL, from 175 µg/mL to 700 µg/mL, from 200 µg/mL to 225 µg/mL, from 200 µg/mL to 250 µg/mL, from 200 µg/mL to 275 µg/mL, from 200 µg/mL to 300 µg/mL, from 200 µg/mL to 325 µg/mL, from 200 µg/mL to 350 µg/mL, from 200 µg/mL to 375 µg/mL, from 200 µg/mL to 400 µg/mL, from 200 µg/mL to 425 µg/mL, from 200 µg/mL to 450 µg/mL, from 200 µg/mL to 475 µg/mL, from 200 µg/mL to 500 µg/mL, from 200 µg/mL to 600 µg/mL, from 200 µg/mL to 700 µg/mL, from 225 µg/mL to 250 µg/mL, from 225 µg/mL to 275 µg/mL, from 225 µg/mL to 300 µg/mL, from 225 µg/mL to 325 µg/mL, from 225 µg/mL to 350 µg/mL, from 225 µg/mL to 375 µg/mL, from 225 µg/mL to 400 µg/mL, from 225 µg/mL to 425 µg/mL, from 225 µg/mL to 450 µg/mL, from 225 µg/mL to 475 µg/mL, from 225 µg/mL to 500 µg/mL, from 225 µg/mL to 600 µg/mL, from 225 µg/mL to 700 µg/mL, from 250 µg/mL to 275 µg/mL, from 250 µg/mL to 300 µg/mL, from 250 µg/mL to 325 µg/mL, from 250 µg/mL to 350 µg/mL, from 250 µg/mL to 375 µg/mL, from 250 µg/mL to 400 µg/mL, from 250 µg/mL to 425 µg/mL, from 250 µg/mL to 450 µg/mL, from 250 µg/mL to 475 µg/mL, from 250 µg/mL to 500 µg/mL, from 250 µg/mL to 600 µg/mL, from 250 µg/mL to 700 µg/mL, from 275 µg/mL to 300 µg/mL, from 275 µg/mL to 325 µg/mL, from 275 µg/mL to 350 µg/mL, from 275 µg/mL to 375 µg/mL, from 275 µg/mL to 400 µg/mL, from 275 µg/mL to 425 µg/mL, from 275 µg/mL to 450 µg/mL, from 275 µg/mL to 475 µg/mL, from 275 µg/mL to 500 µg/mL, from 275

µg/mL to 600 µg/mL, from 275 µg/mL to 700 µg/mL, from 300 µg/mL to 325 µg/mL, from 300 µg/mL to 350 µg/mL, from 300 µg/mL to 375 µg/mL, from 300 µg/mL to 400 µg/mL, from 300 µg/mL to 425 µg/mL, from 300 µg/mL to 450 µg/mL, from 300 µg/mL to 475 µg/mL, from 300 µg/mL to 500 µg/mL, from 300 µg/mL to 600 µg/mL, from 300 µg/mL to 700 µg/mL, from 325 µg/mL to 350 µg/mL, from 325 µg/mL to 375 µg/mL, from 325 µg/mL to 400 µg/mL, from 325 µg/mL to 425 µg/mL, from 325 µg/mL to 450 µg/mL, from 325 µg/mL to 475 µg/mL, from 325 µg/mL to 500 µg/mL, from 325 µg/mL to 600 µg/mL, from 325 µg/mL to 700 µg/mL, from 350 µg/mL to 375 µg/mL, from 350 µg/mL to 400 µg/mL, from 350 µg/mL to 425 µg/mL, from 350 µg/mL to 450 µg/mL, from 350 µg/mL to 475 µg/mL, from 350 µg/mL to 500 µg/mL, from 350 µg/mL to 600 µg/mL, from 350 µg/mL to 700 µg/mL, from 375 µg/mL to 400 µg/mL, from 375 µg/mL to 425 µg/mL, from 375 µg/mL to 450 µg/mL, from 375 µg/mL to 475 µg/mL, from 375 µg/mL to 500 µg/mL, from 375 µg/mL to 600 µg/mL, from 375 µg/mL to 700 µg/mL, from 400 µg/mL to 425 µg/mL, from 400 µg/mL to 450 µg/mL, from 400 µg/mL to 475 µg/mL, from 400 µg/mL to 500 µg/mL, from 400 µg/mL to 600 µg/mL, from 400 µg/mL to 700 µg/mL, from 425 µg/mL to 450 µg/mL, from 425 µg/mL to 475 µg/mL, from 425 µg/mL to 500 µg/mL, from 425 µg/mL to 600 µg/mL, from 425 µg/mL to 700 µg/mL, from 450 µg/mL to 475 µg/mL, from 450 µg/mL to 500 µg/mL, from 450 µg/mL to 600 µg/mL, from 450 µg/mL to 700 µg/mL, from 475 µg/mL to 500 µg/mL, from 475 µg/mL to 600 µg/mL, from 475 µg/mL to 700 µg/mL, from 425 µg/mL to 450 µg/mL, from 425 µg/mL to 475 µg/mL, from 425 µg/mL to 500 µg/mL, from 500 µg/mL to 600 µg/mL, or from 500 µg/mL to 700 µg/mL.

In some embodiments, after electroporation, cells are exposed to concentrations of a selection agent, during culture, for some amount of time to select for cells that have internalized and/or express the selection agent resistance gene. In some aspects during or after selection, selection results in a stable pool of cells. In some instances, cells may be exposed to the selection agent during the selection phase of the process for a predetermined amount of time. In other aspects, the amount of time that cells are exposed to a selection agent while cultured may vary. In some embodiments, cells are exposed to a selection agent for 1, 2, 3, 4, 5, 6, 7, 8, 9, 10, 20, 30, 40, 50, 60, 70, 80, 90 or 100 seconds (or any range derivable therein) of the selection phase, the maintenance/clonal selection phase, clone screening & expansion phase, or large scale-up phase. In other embodiments, cells are exposed to a selection agent while cultured for, for at least, or for at most 1, 2, 3, 4, 5, 6, 7, 8, 9, 10, 20, 30, 40, 50, 60, 70, 80, 90, 100, 110 or 120 minutes (or any range derivable therein) of the selection phase, the maintenance/clonal selection phase, clone screening & expansion phase, or large scale-up phase. In yet other embodiments, cells are exposed to a selection agent while cultured for, for at least, or for at most 1, 2, 3, 4, 5, 6, 7, 8, 9, 10, 11, 12, 13, 14, 15, 16, 17, 18, 19, 20, 21, 22, 23, 24, 36, 48, 60, 72, 84, 96, 108, 120, 132, 144, 156, or 168 hours (or any range derivable therein) of the selection phase, the maintenance/clonal selection phase, clone screening & expansion phase, or large scale-up phase. In yet other aspects, the cells are exposed to the selection agent while cultured for, for at least, or for at most 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, or 60 days (or any range derivable therein) of the selection phase, the maintenance/clonal selection phase, clone screening & expansion phase, or large scale-up phase. In yet other embodiments, the cells are exposed to the selection agent while cultured for, for at least, or for at most for 1, 2, 3, 4, 5, 6, 7, 8, 9, 10, 11, 12, 13, 14, 15, 16, 17, 18, 19, 20, 21, 22, 23, 24, 25, or 26 weeks (or any range derivable therein) of the selection phase, the maintenance/clonal selection phase, clone screening & expansion phase, or large scale-up phase. In certain aspects, the selection phase of the process results in a pool of cells that have stably integrated the electroporated construct in the genome of the cell. In other embodiments, the stable pool of cells represents cells that have stably integrated the electroporated construct. In certain aspects, stable integration represents integration of the entire or some part of the construct into the genome of a cell. In certain aspects, for any contemplated interval of time of culture set forth above, the concentration of the selection agent may be decreased, increased or the selection agent may be changed or omitted.

In certain aspects, after the selection phase, a stable pool of cells are maintained by exposing the cells to concentrations of a selection agent that would compromise the viability of a cell that did not express a selection resistance gene or take up a selection resistance gene during electroporation. In certain aspects the selection agent or compound is an antibiotic. In other aspects the selection agent is G418, puromycin, zeocin, hygromycin, phleomycin or blasticidin, either alone or in combination. In certain aspects the concentration of selection agent during maintenance is in the range of 0.1 µg/L to 0.5 µg/L, 0.5 µg/L to 1 µg/L, 1 µg/L to 2 µg/L, 2 µg/L to 5 µg/L, 5 µg/L to 10 µg/L, 10 µg/L to 100 µg/L, 100 µg/L to 500 µg/L, 0.1 mg/L to 0.5 mg/L, 0.5 mg/L to 1 mg/L, 1 mg/L to 2 mg/L, 2 mg/L to 5 mg/L, 5 mg/L to 10 mg/L, 10 mg/L to 100 mg/L, 100 mg/L to 500 mg/L, 0.1 g/L to 0.5 g/L, 0.5 g/L to 1 g/L, 1 g/L to 2 g/L, 2 g/L to 5 g/L, 5 g/L to 10 g/L, 10 g/L to 100 g/L, or 100 g/L to 500 g/L (or any range derivable therein). In certain aspects the concentration of selection agent during maintenance is (y)g/L, where 'y' can be any value including but not limited to 0.01, 0.02, 0.03, 0.04, 0.05, 0.06, 0.07, 0.08, 0.09, 0.1, 0.15, 0.2, 0.25, 0.3, 0.35, 0.4, 0.45, 0.5, 0.55, 0.6, 0.65, 0.7, 0.75, 0.8, 0.85, 0.9, 0.95, 1, 2, 3, 4, 5, 6, 7, 8, 9, 10, 20, 30, 40, 50, 60, 70, 80, 90, 100 (or any range derivable therein). In some embodiments the selection agent during maintenance is present in the culture media at a concentration of 0.1, 0.2, 0.3, 0.4, 0.5, 0.6, 0.7, 0.8, 0.9, 1, 1.1, 1.2, 1.3, 1.4, 1.5, 1.6, 1.7, 1.8, 1.9, 2, 2.1, 2.2, 2.3, 2.4, 2.5, 2.6, 2.7, 2.8, 2.9, 3, 3.1, 3.2, 3.3, 3.4, 3.5, 3.6, 3.7, 3.8, 3.9, 4, 4.1, 4.2, 4.3, 4.4, 4.5, 4.6, 4.7, 4.8, 4.9, 5, 5.1, 5.2, 5.3, 5.4, 5.5, 5.6, 5.7, 5.8, 5.9, 6, 6.1, 6.2, 6.3, 6.4, 6.5, 6.6, 6.7, 6.8, 6.9, 7, 7.1, 7.2, 7.3, 7.4, 7.5, 7.6, 7.7, 7.8, 7.9, 8, 8.1, 8.2, 8.3, 8.4, 8.5, 8.6, 8.7, 8.8, 8.9, 9, 9.1, 9.2, 9.3, 9.4, 9.5, 9.6, 9.7, 9.8, 9.9, or 10 g/L (or any range derivable therein). In certain aspects the concentration of G418 during maintenance is in the range of 0.1 µg/L to 0.5 µg/L, 0.5 µg/L to 1 µg/L, 1 µg/L to 2 µg/L, 2 µg/L to 5 µg/L, 5 µg/L to 10 µg/L, 10 µg/L to 100 µg/L, 100 µg/L to 500 µg/L, 0.1 mg/L to 0.5 mg/L, 0.5 mg/L to 1 mg/L, 1 mg/L to 2 mg/L, 2 mg/L to 5 mg/L, 5 mg/L to 10 mg/L, 10 mg/L to 100 mg/L, 100 mg/L to 500 mg/L, 0.1 g/L to 0.5 g/L, 0.5 g/L to 1 g/L, 1 g/L to 2 g/L, 2 g/L to 5 g/L, 5 g/L to 10 g/L, 10 g/L to 100 g/L, or 100 g/L to 500 g/L (or any range derivable therein). In certain aspects the concentration of G418 during maintenance is (y)g/L, where 'y' can be any value including but not limited to 0.01, 0.02, 0.03, 0.04, 0.05, 0.06, 0.07, 0.08, 0.09, 0.1, 0.15, 0.2, 0.25, 0.3, 0.35, 0.4, 0.45, 0.5, 0.55, 0.6, 0.65, 0.7, 0.75, 0.8, 0.85, 0.9, 0.95, 1, 2, 3, 4, 5, 6, 7, 8, 9, 10, 20, 30, 40, 50, 60, 70, 80, 90, 100 (or any range derivable therein). In some embodiments the G418 during maintenance is present in the culture media at a concentration of about 0.1, 0.2, 0.3, 0.4, 0.5, 0.6, 0.7, 0.8, 0.9, 1, 1.1, 1.2, 1.3, 1.4, 1.5, 1.6, 1.7, 1.8, 1.9, 2, 2.1, 2.2, 2.3, 2.4, 2.5, 2.6, 2.7, 2.8, 2.9, 3, 3.1, 3.2, 3.3, 3.4, 3.5, 3.6, 3.7, 3.8, 3.9, 4, 4.1, 4.2, 4.3, 4.4, 4.5, 4.6, 4.7, 4.8, 4.9, 5, 5.1, 5.2, 5.3, 5.4, 5.5, 5.6, 5.7, 5.8, 5.9, 6, 6.1, 6.2, 6.3, 6.4, 6.5, 6.6, 6.7, 6.8, 6.9, 7, 7.1, 7.2, 7.3, 7.4, 7.5, 7.6, 7.7, 7.8, 7.9, 8, 8.1, 8.2, 8.3, 8.4, 8.5, 8.6, 8.7, 8.8, 8.9, 9, 9.1, 9.2, 9.3, 9.4, 9.5, 9.6, 9.7, 9.8, 9.9, or 10 g/L or any range derivable therein.

In some embodiments, during or after maintenance, cells may subjected to limiting dilution methods to enable the expansion of clonal populations of cells. The methods of limiting dilution cloning are well known to those of skill in the art. Such methods have been described, for example for hybridomas but can be applied to any cell. Such methods are described in (Cloning hybridoma cells by limiting dilution, Journal of tissue culture methods, 1985, Volume 9, Issue 3, pp 175-177, by Joan C. Rener, Bruce L. Brown, and Roland M. Nardone) which is incorporated by reference herein.

In some embodiments cells are cultured before electroporation or after electroporation. In other embodiments, cells are cultured during the selection phase after electroporation. In yet other embodiments, cells are cultured during the maintenance and clonal selection and initial expansion phase. In still other embodiments, cells are cultured during the screening phase. In other embodiments, cells are cultured during the large scale production phase. Methods of culturing suspension and adherent cells are well-known to those skilled in the art. In some embodiments, cells are cultured in suspension, using commercially available cell-culture vessels and cell culture media. Examples of commercially available culturing vessels that may be used in some embodiments including ADME/TOX Plates, Cell Chamber Slides and Coverslips, Cell Counting Equipment, Cell Culture Surfaces, Corning HYPERFlask Cell Culture Vessels, Coated Cultureware, Nalgene Cryoware, Culture Chamber, Culture Dishes, Glass Culture Flasks, Plastic Culture Flasks, 3D Culture Formats, Culture Multiwell Plates, Culture Plate Inserts, Glass Culture Tubes, Plastic Culture Tubes, Stackable Cell Culture Vessels, Hypoxic Culture Chamber, Petri dish and flask carriers, Quickfit culture vessels, Scale-Up Cell Culture using Roller Bottles, Spinner Flasks, 3D Cell Culture, or cell culture bags.

In other embodiments, media may be formulated using components well-known to those skilled in the art. Formulations and methods of culturing cells are described in detail in the following references: Short Protocols in Cell Biology J. Bonifacino, et al., ed., John Wiley & Sons, 2003, 826 pp; Live Cell Imaging: A Laboratory Manual D. Spector & R. Goldman, ed., Cold Spring Harbor Laboratory Press, 2004, 450 pp.; Stem Cells Handbook S. Sell, ed., Humana Press, 2003, 528 pp.; Animal Cell Culture: Essential Methods, John M. Davis, John Wiley & Sons, Mar. 16, 2011; Basic Cell Culture Protocols, Cheryl D. Helgason, Cindy Miller, Humana Press, 2005; Human Cell Culture Protocols, Series: Methods in Molecular Biology, Vol. 806, Mitry, Ragai R.; Hughes, Robin D. (Eds.), 3rd ed. 2012, XIV, 435 p. 89, Humana Press; Cancer Cell Culture: Method and Protocols, Simon P. Langdon, Springer, 2004; Molecular Cell Biology. 4th edition, Lodish H, Berk A, Zipursky S L, et al., New York: W. H. Freeman; 2000, Section 6.2 Growth of Animal Cells in Culture, all of which are incorporated herein by reference.

In some embodiments, during the screening and expansion phase and/or during the large scale production phase (also referred to as fed-batch & comparison), expanded electroporated cells that result from selection may constitutively express polypeptides derived from exogenously introduced constructs or nucleic acids. In other embodiments, during the screening and expansion phase and/or during the large scale production phase, expanded electroporated cells that result from selection may be induced to express polypeptides derived from exogenously introduced constructs or nucleic acids. In certain aspects, during screening and expansion and/or during large scale production the concentration of expressed polypeptide that results from an exogenously introduced nucleic acid, construct or molecule may be about, at least about, or at most about in the range of 0.1 µg/L to 0.5 µg/L, 0.5 µg/L to 1 µg/L, 1 µg/L to 2 µg/L, 2 µg/L to 5 µg/L, 5 µg/L to 10 µg/L, 10 µg/L to 100 µg/L, 100 µg/L to 500 µg/L, 0.1 mg/L to 0.5 mg/L, 0.5 mg/L to 1 mg/L, 1 mg/L to 2 mg/L, 2 mg/L to 5 mg/L, 5 mg/L to 10 mg/L, 10 mg/L to 100 mg/L, 100 mg/L to 500 mg/L, 0.1 g/L to 0.5 g/L, 0.5 g/L to 1 g/L, 1 g/L to 2 g/L, 2 g/L to 5 g/L, 5 g/L to 10 g/L, 10 g/L to 100 g/L, or 100 g/L to 500 g/L, or any range derivable therein. In other embodiments, the concentration of expressed polypeptide that results from an exogenously introduced nucleic acid, construct or molecule may be 0.1, 0.15, 0.2, 0.25, 0.3, 0.35, 0.4, 0.45, 0.5, 0.55, 0.6, 0.65, 0.7, 0.75, 0.8, 0.85, 0.9, 0.95, 1, 2, 3, 4, 5, 6, 7, 8, 9, 10, 11, 12, 13, 14, 15, 16, 17, 18, 19, 20 10, 20, 30, 40, 50, 60, 70, 80, 90, 100, 110, 120, 130, 140, 150, 160, 170, 180, 190, 200, 210, 220, 230, 240, 250 100, 200, 300, 400, 500, 600, 700, 800, 900, 1000, 1100, 1200, 1300, 1400, 1500, 1600, 1700, 1800, 1900, 2000, 2100, 2200, 2300, 2400, 2500, 2600, 2700, 2800, 2900, 3000, 3100, 3200, 3300, 3400, 3500, 3600, 3700, 3800, 3900, 4000, 4100, 4200, 4300, 4400, 4500, 4600, 4700, 4800, 4900, 5000, 5000, 5250, 5500, 5750, 6000, 6250, 6500, 6750, 7000, 7250, 7500, 7750, 8000, 8250, 8500, 8750, 9000, 9250, 9500, 9750, or 10000 mg/L, or any range derivable therein.

IV. Proteinaceous Compositions

In some embodiments, cells are electroporated with nucleic acids, nucleic acid constructs or vectors that provide means of heterologous expression that includes, but is not limited to, cloned genes, modified cloned genes, recombinant genes, fusion proteins, cassettes, open reading frames or expressed sequence tags. In certain embodiments, electroporated cells express or are capable of expressing including, but not limited to, secreted proteins, surface receptors, membrane proteins, cytoplasmic proteins, GPCRs, ion channels, nuclear receptors, kinases or aptamers. In specific embodiments, electroporated cells express antibodies. In other embodiments the electroporated cells express an antibody fusion protein, wherein the recombinant nucleic acid encoding the antibody is fused to another nucleic acid that encodes another polypeptide. In yet other embodiments the electroporated cell is a stably transfected electroporated cell.

The claimed methods can be used to introduce any genetic material into a cell or cell fragment. The genetic material may code for a specific protein or may be an antisense genetic material. Examples of proteins and peptides that can be introduced into host cells by introducing the expression vector that codes for that protein or peptide include, but is not limited to, genes that code for b-cell differentiation factors, b-cell growth factors, mitogenic cytokines, chemotactic cytokines, colony stimulating factors, angiogenesis factors, adhesion factors (cadherins, selecting, integrins, NCAMs, ICAMs, and L1) t-cell replacing factors, differentiation factors, transcription factors, mRNA, heat shock proteins, nuclear protein complexes, and RNA/DNA oligomers. Nucleic acids encoding specific factors that can be introduced into a host cell using the flow electroporation system of the present invention include, but are not limited to, IFN-alpha, IFN-beta, IFN-omega, IL1, IL2, IL3, IL4, IL5, IL6, IL7, IL8, IL9, IL10, IL11, IL12, IL13, IL14, IL15, IL16, IL17, IL18, leptin, myostatins (growth differentiation factors), macrophage stimulating protein and derivatives thereof, platelet-derived growth factor, tumor necrosis factors (TNF-alpha, TNF-beta, NGF, CD40L, CD137L/4-1BBL, human lymphotoxin-beta, TNF-related apoptosis-inducing ligand (trail)), monoclonal antibodies, G-CSF, M-CSF, GM-CSF, PDGF, IL1-alpha, IL1-beta, FGF IFN-gamma, IP-10, PF4, GRO, and 9E3, erythropoietin (EPO), endostatin and fragments thereof, angiostatin and fragments thereof, fibroblast growth factors (FGF), VEGF, soluble receptors and any fragments or combinations thereof.

V. Nucleic Acids

In certain embodiments, there are recombinant polynucleotides encoding the proteins, polypeptides, or peptides described herein. Polynucleotide sequences contemplated include those encoding antibodies or binding portions thereof.

As used in this application, the term "polynucleotide" refers to a nucleic acid molecule that either is recombinant or has been isolated free of total genomic nucleic acid. Included within the term "polynucleotide" are oligonucleotides (nucleic acids 100 residues or less in length), recombinant vectors, including, for example, plasmids, cosmids, phage, viruses, and the like. Polynucleotides include, in certain aspects, regulatory sequences, isolated substantially away from their naturally occurring genes or protein encoding sequences. Polynucleotides may be single-stranded (coding or antisense) or double-stranded, and may be RNA, DNA (genomic, cDNA or synthetic), analogs thereof, or a combination thereof. Additional coding or non-coding sequences may, but need not, be present within a polynucleotide.

In this respect, the term "gene," "polynucleotide," or "nucleic acid" is used to refer to a nucleic acid that encodes a protein, polypeptide, or peptide (including any sequences required for proper transcription, post-translational modification, or localization). As will be understood by those in the art, this term encompasses genomic sequences, expression cassettes, cDNA sequences, and smaller engineered nucleic acid segments that express, or may be adapted to express, proteins, polypeptides, domains, peptides, fusion proteins, and mutants. A nucleic acid encoding all or part of a polypeptide may contain a contiguous nucleic acid sequence encoding all or a portion of such a polypeptide. It also is contemplated that a particular polypeptide may be encoded by nucleic acids containing variations having slightly different nucleic acid sequences but, nonetheless, encode the same or substantially similar protein (see above).

In particular embodiments, there are isolated nucleic acid segments and recombinant vectors incorporating nucleic acid sequences that encode a polypeptide (e.g., an antibody or fragment thereof). The term "recombinant" may be used in conjunction with a polypeptide or the name of a specific polypeptide, and this generally refers to a polypeptide produced from a nucleic acid molecule that has been manipulated in vitro or that is a replication product of such a molecule.

The nucleic acid segments, regardless of the length of the coding sequence itself, may be combined with other nucleic acid sequences, such as promoters, polyadenylation signals, additional restriction enzyme sites, multiple cloning sites, other coding segments, and the like, such that their overall length may vary considerably. It is therefore contemplated that a nucleic acid fragment of almost any length may be employed, with the total length preferably being limited by the ease of preparation and use in the intended recombinant nucleic acid protocol. In some cases, a nucleic acid sequence may encode a polypeptide sequence with additional heterologous coding sequences, for example to allow for purification of the polypeptide, transport, secretion, post-translational modification, or for therapeutic benefits such as targeting or efficacy. As discussed above, a tag or other heterologous polypeptide may be added to the modified polypeptide-encoding sequence, wherein "heterologous" refers to a polypeptide that is not the same as the modified polypeptide.

A. Vectors

Polypeptides may be encoded by a nucleic acid molecule. The nucleic acid molecule can be in the form of a nucleic acid vector. The term "vector" is used to refer to a carrier nucleic acid molecule into which a heterologous nucleic acid sequence can be inserted for introduction into a cell where it can be replicated and expressed. A nucleic acid sequence can be "heterologous," which means that it is in a context foreign to the cell in which the vector is being introduced or to the nucleic acid in which is incorporated, which includes a sequence homologous to a sequence in the cell or nucleic acid but in a position within the host cell or nucleic acid where it is ordinarily not found. Vectors include DNAs, RNAs, plasmids, cosmids, viruses (bacteriophage, animal viruses, and plant viruses), and artificial chromosomes (e.g., YACs). One of skill in the art would be well equipped to construct a vector through standard recombinant techniques (for example Sambrook et al., 2001; Ausubel et al., 1996, both incorporated herein by reference). Vectors may be used in a host cell to produce an antibody.

The term "expression vector" refers to a vector containing a nucleic acid sequence coding for at least part of a gene product capable of being transcribed or stably integrate into a host cell's genome and subsequently be transcribed. In some cases, RNA molecules are then translated into a protein, polypeptide, or peptide. Expression vectors can contain a variety of "control sequences," which refer to nucleic acid sequences necessary for the transcription and possibly translation of an operably linked coding sequence in a particular host organism. In addition to control sequences that govern transcription and translation, vectors and expression vectors may contain nucleic acid sequences that serve other functions as well and are described herein.

A "promoter" is a control sequence. The promoter is typically a region of a nucleic acid sequence at which initiation and rate of transcription are controlled. It may contain genetic elements at which regulatory proteins and molecules may bind such as RNA polymerase and other transcription factors. The phrases "operatively positioned," "operatively linked," "under control," and "under transcriptional control" mean that a promoter is in a correct functional location and/or orientation in relation to a nucleic acid sequence to control transcriptional initiation and expression of that sequence. A promoter may or may not be used in conjunction with an "enhancer," which refers to a cis-acting regulatory sequence involved in the transcriptional activation of a nucleic acid sequence.

The particular promoter that is employed to control the expression of a peptide or protein encoding polynucleotide is not believed to be critical, so long as it is capable of expressing the polynucleotide in a targeted cell, preferably a bacterial cell. Where a human cell is targeted, it is preferable to position the polynucleotide coding region adjacent to and under the control of a promoter that is capable of being expressed in a human cell. Generally speaking, such a promoter might include either a bacterial, human or viral promoter.

A specific initiation signal also may be required for efficient translation of coding sequences. These signals include the ATG initiation codon or adjacent sequences. Exogenous translational control signals, including the ATG initiation codon, may need to be provided. One of ordinary skill in the art would readily be capable of determining this and providing the necessary signals.

Vectors can include a multiple cloning site (MCS), which is a nucleic acid region that contains multiple restriction enzyme sites, any of which can be used in conjunction with standard recombinant technology to digest the vector. (See Carbonelli et al., 1999, Levenson et al., 1998, and Cocea, 1997, incorporated herein by reference.)

Most transcribed eukaryotic RNA molecules will undergo RNA splicing to remove introns from the primary transcripts. Vectors containing genomic eukaryotic sequences may require donor and/or acceptor splicing sites to ensure proper processing of the transcript for protein expression. (See Chandler et al., 1997, incorporated herein by reference.)

The vectors or constructs will generally comprise at least one termination signal. A "termination signal" or "terminator" is comprised of the DNA sequences involved in specific termination of an RNA transcript by an RNA polymerase. Thus, in certain embodiments a termination signal that ends the production of an RNA transcript is contemplated. A terminator may be necessary in vivo to achieve desirable message levels. In eukaryotic systems, the terminator region may also comprise specific DNA sequences that permit site-specific cleavage of the new transcript so as to expose a polyadenylation site. This signals a specialized endogenous polymerase to add a stretch of about 200 A residues (polyA) to the 3' end of the transcript. RNA molecules modified with this polyA tail appear to more stable and are translated more efficiently. Thus, in other embodiments involving eukaryotes, it is preferred that that terminator comprises a signal for the cleavage of the RNA, and it is more preferred that the terminator signal promotes polyadenylation of the message.

In expression, particularly eukaryotic expression, one will typically include a polyadenylation signal to effect proper polyadenylation of the transcript.

In order to propagate a vector in a host cell, it may contain one or more origins of replication sites (often termed "ori"), which is a specific nucleic acid sequence at which replication is initiated. Alternatively an autonomously replicating sequence (ARS) can be employed if the host cell is yeast.

Some vectors may employ control sequences that allow it to be replicated and/or expressed in both prokaryotic and eukaryotic cells. One of skill in the art would further understand the conditions under which to incubate all of the above described host cells to maintain them and to permit replication of a vector. Also understood and known are techniques and conditions that would allow large-scale production of vectors, as well as production of the nucleic acids encoded by vectors and their cognate polypeptides, proteins, or peptides.

B. Expression of Nucleic Acid Constructs

Substitutional variants typically contain the exchange of one amino acid for another at one or more sites within the protein, and may be designed to modulate one or more properties of the polypeptide, with or without the loss of other functions or properties. Substitutions may be conservative, that is, one amino acid is replaced with one of similar shape and charge. Conservative substitutions are well known in the art and include, for example, the changes of: alanine to serine; arginine to lysine; asparagine to glutamine or histidine; aspartate to glutamate; cysteine to serine; glutamine to asparagine; glutamate to aspartate; glycine to proline; histidine to asparagine or glutamine; isoleucine to leucine or valine; leucine to valine or isoleucine; lysine to arginine; methionine to leucine or isoleucine; phenylalanine to tyrosine, leucine or methionine; serine to threonine; threonine to serine; tryptophan to tyrosine; tyrosine to tryptophan or phenylalanine; and valine to isoleucine or leucine. Alternatively, substitutions may be non-conservative such that a function or activity of the polypeptide is affected. Non-conservative changes typically involve substituting a residue with one that is chemically dissimilar, such as a polar or charged amino acid for a nonpolar or uncharged amino acid, and vice versa.

Proteins may be recombinant, or synthesized in vitro. Alternatively, a non-recombinant or recombinant protein may be isolated from bacteria. It is also contemplated that a bacteria containing such a variant may be implemented in compositions and methods. Consequently, a protein need not be isolated.

The term "functionally equivalent codon" is used herein to refer to codons that encode the same amino acid, such as the six codons for arginine or serine, and also refers to codons that encode biologically equivalent amino acids (see Table 1, below).

| Codon Table | | | |
|---|---|---|---|
| Amino Acids | | | Codons |
| Alanine | Ala | A | GCA GCC GCG GCU |
| Cysteine | Cys | C | UGC UGU |
| Aspartic acid | Asp | D | GAC GAU |
| Glutamic acid | Glu | E | GAA GAG |
| Phenylalanine | Phe | F | UUC UUU |
| Glycine | Gly | G | GGA GGC GGG GGU |
| Histidine | His | H | CAC CAU |
| Isoleucine | Ile | I | AUA AUC AUU |
| Lysine | Lys | K | AAA AAG |
| Leucine | Leu | L | UUA UUG CUA CUC CUG CUU |
| Methionine | Met | M | AUG |
| Asparagine | Asn | N | AAC AAU |
| Proline | Pro | P | CCA CCC CCG CCU |
| Glutamine | Gln | Q | CAA CAG |
| Arginine | Arg | R | AGA AGG CGA CGC CGG CGU |
| Serine | Ser | S | AGC AGU UCA UCC UCG UCU |
| Threonine | Thr | T | ACA ACC ACG ACU |
| Valine | Val | V | GUA GUC GUG GUU |

-continued

Codon Table

| Amino Acids | | | Codons |
|---|---|---|---|
| Tryptophan | Trp | W | UGG |
| Tyrosine | Tyr | Y | UAC UAU |

It also will be understood that amino acid and nucleic acid sequences may include additional residues, such as additional N- or C-terminal amino acids, or 5' or 3' sequences, respectively, and yet still be essentially as set forth in one of the sequences disclosed herein, so long as the sequence meets the criteria set forth above, including the maintenance of biological protein activity where protein expression is concerned. The addition of terminal sequences particularly applies to nucleic acid sequences that may, for example, include various non-coding sequences flanking either of the 5' or 3' portions of the coding region.

The following is a discussion based upon changing of the amino acids of a protein to create an equivalent, or even an improved, second-generation molecule. For example, certain amino acids may be substituted for other amino acids in a protein structure without appreciable loss of interactive binding capacity with structures such as, for example, antigen-binding regions of antibodies or binding sites on substrate molecules. Since it is the interactive capacity and nature of a protein that defines that protein's biological functional activity, certain amino acid substitutions can be made in a protein sequence, and in its underlying DNA coding sequence, and nevertheless produce a protein with like properties. It is thus contemplated by the inventors that various changes may be made in the DNA sequences of genes without appreciable loss of their biological utility or activity.

In making such changes, the hydropathic index of amino acids may be considered. The importance of the hydropathic amino acid index in conferring interactive biologic function on a protein is generally understood in the art (Kyte and Doolittle, 1982). It is accepted that the relative hydropathic character of the amino acid contributes to the secondary structure of the resultant protein, which in turn defines the interaction of the protein with other molecules, for example, enzymes, substrates, receptors, DNA, antibodies, antigens, and the like.

It also is understood in the art that the substitution of like amino acids can be made effectively on the basis of hydrophilicity. U.S. Pat. No. 4,554,101, incorporated herein by reference, states that the greatest local average hydrophilicity of a protein, as governed by the hydrophilicity of its adjacent amino acids, correlates with a biological property of the protein. It is understood that an amino acid can be substituted for another having a similar hydrophilicity value and still produce a biologically equivalent and immunologically equivalent protein.

As outlined above, amino acid substitutions generally are based on the relative similarity of the amino acid side-chain substituents, for example, their hydrophobicity, hydrophilicity, charge, size, and the like. Exemplary substitutions that take into consideration the various foregoing characteristics are well known and include: arginine and lysine; glutamate and aspartate; serine and threonine; glutamine and asparagine; and valine, leucine and isoleucine.

Antibodies

In some particular embodiments, "antibody" as used herein includes intact immunoglobulin molecules, fragments of immunoglobulins, aptamers, and polypeptides that have been engineered to have an antibody-like binding site, which are capable of binding an epitope of any type of target molecule. Any type of antibody known in the art can be generated to bind specifically to an antigen epitope.

An antibody is an immunoglobulin which possesses the ability to combine with an antigen. It comprises at least two heavy (H) chains and two light (L) chains inter-connected by disulfide bonds. Non-limiting examples of antibodies include monoclonal antibodies (e.g., full length or intact monoclonal antibodies), polyclonal antibodies, multivalent antibodies, and multi-specific antibodies (e.g., bi-specific antibodies as long as they exhibit the desired biological activity). An antibody can be affinity-matured.

The term "antibody fragment" comprises only a portion of an intact antibody, wherein the portion preferably retains at least one, preferably most or all, of the functions normally associated with that portion when present in an intact antibody. Examples of antibody fragments include Fab, Fab', F(ab')2, and Fv fragments; linear antibodies; single-chain antibody molecules; and multispecific antibodies formed from antibody fragments. In one embodiment, an antibody fragment comprises an antigen binding site of the intact antibody and thus retains the ability to bind antigen. In another embodiment, an antibody fragment, for example one that comprises the Fc region, retains at least one of the biological functions normally associated with the Fc region when present in an intact antibody. For example, such an antibody fragment may comprise an antigen-binding arm linked to a sequence capable of conferring stability to the fragment.

An "isolated" or "purified" antibody is one which has been identified and separated or recovered, or both, from a component of its natural environment. Contaminant components of an isolated antibody's natural environment are materials that would interfere with diagnostic uses of the antibody. Non-limiting examples of such contaminants include enzymes, hormones, and other proteinaceous or non-proteinaceous solutes. In some embodiments, for example, the antibody may be purified to greater than 95% by weight of protein as determined by the Lowry method, and sometimes more than 99% by weight. Isolated antibody includes the antibody in situ within recombinant cells because at least one component of the antibody's natural environment will not be present. Ordinarily, however, isolated antibody will be prepared by at least one purification step.

The terms "monoclonal antibody" or "monoclonal antibody composition" as used herein refer to a preparation of antibody molecules of single molecular composition. A monoclonal antibody composition displays a single binding specificity and affinity for a particular epitope. The monoclonal antibodies herein specifically include "chimeric" antibodies in which a portion of the heavy or light chain, or both, is identical with or homologous to corresponding sequences in antibodies derived from a particular species or belonging to a particular antibody class or subclass, while the remainder of the chain or chains are identical with or homologous to corresponding sequences in antibodies derived from another species or belonging to another antibody class or subclass, as well as fragments of such antibodies so long as they exhibit the desired biological activity.

"Single-chain Fv" or "scFv" antibody fragments comprise the $V_H$ and $V_L$ domains of antibody, wherein these domains are present in a single polypeptide chain. Generally, the scFv polypeptide further comprises a polypeptide linker between the $V_H$ and $V_L$ domains which enables the scFv to form the desired structure for antigen binding.

An "antigen" is a predetermined substance to which an antibody can selectively bind. The target antigen may be polypeptide, carbohydrate, nucleic acid, lipid, hapten or other naturally occurring or synthetic compound. In some embodiments herein, the relevant antigen is any member protein of the N-methyl-2 superfamily, occurring as either 1) a single protein in solution, 2) a constituent of a complex of proteins, 3) a constituent of a fragment of a cell, or 4) an intact cell.

An "epitope" is the portion of the antigen to which the antibody selectively binds. For a polypeptide antigen, the epitope is generally a peptide portion of about four to ten amino acids.

A "cross-reactive antibody", as used herein, is an antibody that can bind to multiple proteins that differ in primary amino acid sequence. Cross-reactive antibodies bind to multiple proteins having related amino acid sequences, yet do not bind to other proteins with sufficiently distinct amino acid sequences or proteins having sufficiently modified compositions, for example by chemical modification. Cross-reactive antibodies may be polyclonal or monoclonal, aptamers, or fragments including Fab, Fab', F(ab')2, and Fv. Examples of cross-reactive antibodies were known even in the early work on antibodies (Landsteiner K. The Specificity of Serological Reactions, rev. edn. New York: Dover, 1962). As one example, the field of tissue histocompatibility typing was developed using cross-reactive polyclonal antibodies that bound to overlapping sets of homologous but variable major histocompatibility complex (MHC) determinants (*Histocompatibility Testing: Report of a Conference and Workshop. Washington D.C.: National Academy of Sciences—National Research Council*, 1965.) Later work determined specific sequences bound by each polyclonal antibody and defined the cross-reactivity profile of each antibody at the amino acid sequence level (*Dupont B, ed. Immunobiology of HLA. Histocompatibility Testing* 1987, *Vol. I, and Immunogenetics and Histocompatibility, Vol II*. Springer-Verlag, New York, 1988.) It was found that, in many cases, a single amino acid substitution abrogated binding by some cross-reactive antibodies, while in other cases a variety of substitutions had negligible effects on binding. Similar results were also demonstrated for cross-reactive monoclonal antibodies to MHC determinants (Parham P, Brodsky F M. Partial purification and some properties of BB7.2. A cytotoxic monoclonal antibody with specificity for HLA-A2 and a variant of HLA-A28. Hum Immunol. 1981 December; 3(4):277-99.)

Monoclonal antibodies produced by any means may be further purified, if desired, using any technique known to those of ordinary skill in the art, such as filtration, centrifugation and various chromatographic methods such as FPLC or affinity chromatography or any other method known to those of ordinary skill in the art.

Nucleic acids encoding antibody gene fragments may be obtained from immune cells harvested from humans or animals. If a library biased in favor of specific clones is desired, the subject is immunized with the antigen to generate an antibody response, and spleen cells and/or circulating B cells or other peripheral blood lymphocytes (PBLs) are recovered for library construction. Additional enrichment for specifically reactive cell populations can be obtained by using a suitable screening procedure to isolate B cells expressing specific membrane bound antibody. Alternatively, the use of spleen cells and/or B cells or other PBLs from an unimmunized donor provides a better representation of the possible antibody repertoire, and also permits the construction of an antibody library using any animal (human or non-human) species in which the antigen is not antigenic. For libraries incorporating in vitro antibody gene construction, stem cells are harvested from the subject to provide nucleic acids encoding unrearranged antibody gene segments. The immune cells of interest can be obtained from a variety of animal species, such as human, mouse, rat, etc. Nucleic acid encoding antibody variable gene segments are recovered from the cells of interest and amplified.

Nucleic acid sequence encoding a polypeptide can be designed using the amino acid sequence of the desired region of the polypeptide. Alternatively, the cDNA sequence (or fragments thereof) may be used. DNAs encoding the polypeptide can be prepared by a variety of methods known in the art. Following construction of the DNA molecule encoding the polypeptide, the DNA molecule is operably linked to an expression control sequence in an expression vector, such as a plasmid, wherein the control sequence is recognized by a host cell transformed with the vector. Suitable vectors for expression in prokaryotic and eukaryotic host cells are known in the art. Optionally, the DNA encoding the polypeptide is operably linked to a secretory leader sequence resulting in secretion of the expression product by the host cell into the culture medium. Host cells are transfected and preferably transformed with the expression or cloning vectors of this invention and cultured in conventional nutrient media modified as appropriate for inducing promoters, selecting transformants, or amplifying the genes encoding the desired sequences.

The purified polypeptide can be attached to a suitable matrix such as agarose beads, acrylamide beads, glass beads, cellulose, various acrylic copolymers, hydroxyl methacrylate gels, polyacrylic and polymethacrylic copolymers, nylon, neutral and ionic carriers, and the like, for use in the affinity chromatographic separation of phage display clones. Alternatively, the protein can be used to coat the wells of adsorption plates, expressed on host cells affixed to adsorption plates or used in cell sorting, or conjugated to biotin for capture with streptavidin-coated beads, or used in any other art-known method for panning phage display libraries. The phage library samples are contacted with the immobilized protein under conditions suitable for binding of at least a portion of the phage particles with the adsorbent. Normally, the conditions, including pH, ionic strength, temperature and the like are selected to mimic physiological conditions. The phages bound to the solid phase are washed and then eluted. Moreover, the enriched phages can be grown in bacterial culture and subjected to further rounds of selection.

DNA encoding the hybridoma-derived monoclonal antibodies or phage display Fv clones of the invention is readily isolated and sequenced using conventional procedures (e.g. by using oligonucleotide primers designed to specifically amplify the heavy and light chain coding regions of interest from hybridoma or phage DNA template). Once isolated, the DNA can be placed into expression vectors, which are then transfected into host cells such as *E. coli* cells, simian COS cells, Chinese hamster ovary (CHO) cells, or myeloma cells that do not otherwise produce immunoglobulin protein, to obtain the synthesis of the desired monoclonal antibodies in the recombinant host cells.

DNA encoding the Fv clones of the invention can be combined with known DNA sequences encoding heavy chain and/or light chain constant regions (e.g. the appropriate DNA sequences can be obtained from Kabat et al., supra) to form clones encoding full or partial length heavy and/or light chains. It will be appreciated that constant regions of any isotype can be used for this purpose, including IgG, IgM, IgA, IgD, and IgE constant regions, and that such constant regions can be obtained from any human or animal species. A Fv clone derived from the variable domain DNA of one animal (such as human) species and then fused to constant region DNA of another animal species to form coding sequence(s) for "hybrid," full length heavy chain and/or light chain is included in the definition of "chimeric" and "hybrid" antibody as used herein. In a preferred embodiment, a Fv clone derived from human variable DNA is fused to human constant region DNA to form coding sequence(s) for all human, full or partial length heavy and/or light chains.

DNA encoding the antibody derived from a hybridoma of the invention can also be modified, for example, by substituting the coding sequence for human heavy- and light-chain constant domains in place of homologous murine sequences derived from the hybridoma clone. DNA encoding a hybridoma or Fv clone-derived antibody or fragment can be further modified by covalently joining to the immunoglobulin coding sequence all or part of the coding sequence for a non-immunoglobulin polypeptide. In this manner, "chimeric" or "hybrid" antibodies are prepared that have the binding specificity of the Fv clone or hybridoma clone-derived antibodies of the invention.

1. Antibody Fragments

In some embodiments, the present invention encompasses antibody fragments. In certain circumstances there are advantages of using antibody fragments, rather than whole antibodies.

Non-limiting examples of antibody fragments include Fab, Fab', Fab'-SH and F(ab')2 fragments of the antibodies provided herein. These antibody fragments can be created by traditional means, such as enzymatic digestion, or may be generated by recombinant techniques. These fragments are useful for the diagnostic purposes set forth below.

Various techniques may be used for the production of antibody fragments. Traditionally, these fragments were derived via proteolytic digestion of intact antibodies, such as with pepsin or papain and/or by cleavage of disulfide bonds by chemical reduction. However, these fragments can now be produced directly by recombinant host cells. For example, Fab, Fv and ScFv antibody fragments can all be expressed in and secreted from E. coli, thus allowing the facile production of large amounts of these fragments. Alternatively, monoclonal antibody fragments encompassed by the present invention can be synthesized using an automated peptide synthesizer.

Aptamers are nucleic acid molecules that may be engineered through repeated rounds of in vitro selection to bind to various targets including, for example, proteins, nucleic acids, cells, tissues, and organisms. Because of their specificity and binding abilities, aptamers have great potential as diagnostic agents. In some cases, aptamers have been shown to be better diagnostic agents than other molecules, such as antibodies. An additional advantage of using aptamers is that mass production does not require either animal or cultured cells. Aptamer synthesis may be conducted through Polymerase Chain Reaction ("PCR") or oligonucleotide synthesis, and the resulting aptamers are stable at room temperature and have a long shelf life.

Development of aptamers is typically done through SELEX (Systematic Evolution of Ligands by Exponential Enrichment) or variations on the SELEX process. The SELEX process has been described by Turek and Gold, 1990, and in U.S. Pat. Nos. 5,270,163 and 5,475,096, which are incorporated herein by reference. Variations on the SELEX process, such as photo-SELEX, counter-SELEX, chemi-SELEX, chimeric-SELEX, blended-SELEX, and automated-SELEX, have also been reported. Through SELEX, a large population of oligonucleotides is allowed to interact with the target of interest (e.g., a bacteria cell or a protein isolated from the surface of a bacteria cell). Molecules which bind to the target (termed successful) are separated from those that do not bind through one of several techniques. For example, aptamer bound targets may be removed from the population through binding to nitrocellulose, affinity chromatography, etc. The bound aptamers may then be amplified by PCR.

Screening Methods

Embodiments further comprise methods for identifying an antibody capable of binding a specific protein. These assays may comprise screening of large libraries of candidate substances; alternatively, the assays may be used to focus on particular classes of compounds selected with an eye towards structural attributes that are believed to make them more likely to bind a specific protein.

By screening, it is meant that one may assay a series of candidate substances for the ability to bind a specific protein. To identify an antibody with this property, as is used in some embodiments, one generally will perform an immunoassay using a preparation known to comprise a known specific protein, fragments thereof, or synthetic constructs comprising particular epitopes thereof.

This immunoassay will further comprise methods to detect the occurrence of binding between a candidate antibody and the said preparation. Examples of methods useful in identifying antibodies having bound a specific protein include: ELISA, RIA, CLIA, fluorescence assays, and label-free binding assays wherein unbound antibody is removed by washing steps and only antibodies which have bound to a target protein remain attached to a solid support. Many analogous methods are known by those of moderate skill in the art. Analogous methods can also be used to identify suitable antibody fragments, including scFv, and aptamers.

Those of moderate skill in the art recognize that other sequential screening methods and other assay formats may also be used to achieve substantially identical results. Conversely, antibodies can be screened to select for binding to specific proteins but not others.

When a specific embodiment of the disclosure includes a range, as described herein, it is specifically contemplated that ranges and specific values (i.e. concentrations) may be excluded in embodiments of the invention. It is also contemplated that, when the disclosure includes a list of elements (e.g. cell types), embodiments of the invention may specifically exclude one or more elements in the list.

VI. Examples

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1—Rapid High Expressing Stable Cell Line Development with MaxCyte STX Transfection Technology Materials and Methods Cells: CHO-S cells were purchased from LifeTechnology (Cat. No. A1155701) and grown in CD CHO media (Lifetech. Cat. No. 10743029) supplemented with 1×HT solution (LifeTech. Cat. No. 11067-030) and 2 mM GlutaMax (LifeTech. Cat. No. 35050-061). Cells were maintained in the linear log growth phase to keep healthy cells for the transfection.

Transfection: At the day prior to transfection, cells were scaled up to the needed volume to have enough cells for next day transfection. For GFP transfection, GFP cDNA was cloned in to a plasmid vector pCI (Promega) with expression of GFP driven by the human cytomegalovirus (CMV) immediate-early gene enhancer/promoter region. For antibody, heavy chain and light chain of humanized IgG1 cDNAs were cloned in to the same pcDNA3.1 vector. The antibody expression vector was linearized with a single enzyme cut for stable transfection. Transfection was carried out by using 80 μg linearized DNA and 80E6 CHO-S cells in 400 μl EP Buffer with MaxCyte STX transfection technology. Briefly, the needed cells were spun down and re-suspended in MaxCyte electroporation buffer. The cells were then mixed with the DNA well and cells/DNA mixture was loaded in to an OC-400 cuvette for the transfection. The transfected cells were transferred to a 125 ml Erlenmeyer shake flask for recovery in the incubator at 37° C. for 40 minutes. The CD CHO supplemented media was then added to the transfected cells.

Selection and cloning: Twenty four hours post EP, stable selection was started. Cells were spun down and then re-suspended in the selection media which was the supplemented CD CHO media containing 1.6 g/L G418. The clones were observed in two weeks in the selection media and then limiting dilution cloning as 0.3 cell per well in 96 well plates was initiated. Clone screening by using Elisa assay started when the clones were developed.

Elisa Assay: Elisa assay was used to screen and identify the high expressing clones. Goat Anti-Human IgG, Fcγ Fragment (Sigma, cat#: 12136-1 ml) was diluted to 2 μg/ml in carbonate buffer (sigma, C3041-100CAP) and then plates were coated with 50 μl of diluted capture antibody at 4° C. overnight. Plates were washed three times with PBS/0.1% Tween20 and then blocked with 200 μl of PBS/0.1% Tween20/BSA at 4° C. overnight. Diluted samples were added to the plates and human IgG1 (Sigma, I5154-1 mg) was diluted as a serial dilution and used for a standard curve. The incubation was carried out at room temperature for 1 hour and then plates were washed three times with PBS/0.1% Tween. The Peroxidase-Conjugated Rabbit Anti-human IgG(H+L) (Sigma, A8792-2 ml) was diluted as 1:20,000 and added as 50 μl per well. The plates were incubated at room temperate 1 hour and washed as above. One hundred microliters of TMB substrate (Sigma, T8665) were added per well, incubated at room temperature about 5 minutes and stopped by 50 μl of 0.25M sulfuric acid (Sigma, 38295-1EA). The data were read out by a microplate Elisa reader (FLUOstar OPTIMA).

Results

FIG. 1 shows the work flow diagram of the stable cell line production process. After electroporation, cells may be cultured for some period of time without selection to allow for recovery from the electroporation procedure (not depicted in figure). After electroporation, cells are selected for by culturing cells in the presence of a selection agent (selection phase). After the selection phase, cells are cultured at lower density in the presence of selection agent to enable limiting dilution cloning (maintenance/clonal selection phase). After the generation of clonal populations, clones are screened for exogenous polypeptide expression and expanded (clonal screening and expansion phase). After screening, clones with desired activity are grown on larger scale for production purposes (large scale-up phase) or submitted to long-term storage such as cryopreservation (FIG. 1).

Figure 2:
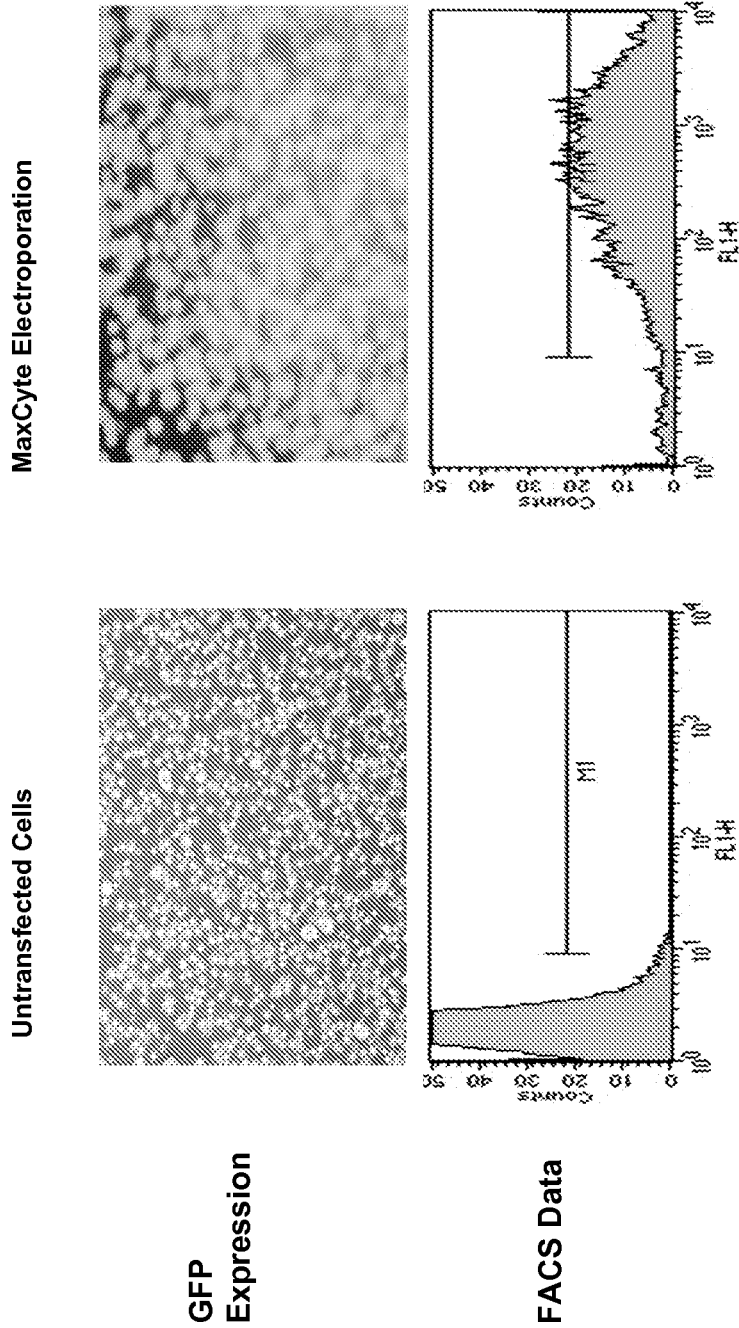
FIG. 2: Greater than 95% CHO Cell Transfection Efficiency and Cell Viability using MaxCyte Static and Flow Electroporation. CHO-S cells were transfected with a plasmid encoding green fluorescent protein (1 μg DNA/1E6 cells) using small scale, static electroporation on the MaxCyte STX. GFP expression and viability were measured by flow cytometry (FACS) 24 hours post electroporation. Both transfection efficiency and cell viability were >95%.

STX technology is able to transfect many difficult to transfect cell lines with very high transfection efficiency and cell viability including CHO cells (FIG. 2). This unique feature allowed us to develop a high stringent selection process for the stable cell lime generation. We used 1.6 g/L G418 concentration and successfully and quickly develop a stable cell line with >3 g/L productivity. Thus far, there have been no reports showing the success rate and efficiency with such high G418 selection pressure for mammalian stable cell line development by using other transfection methods (Naoko 2004; Kim 2012).

Figure 3:
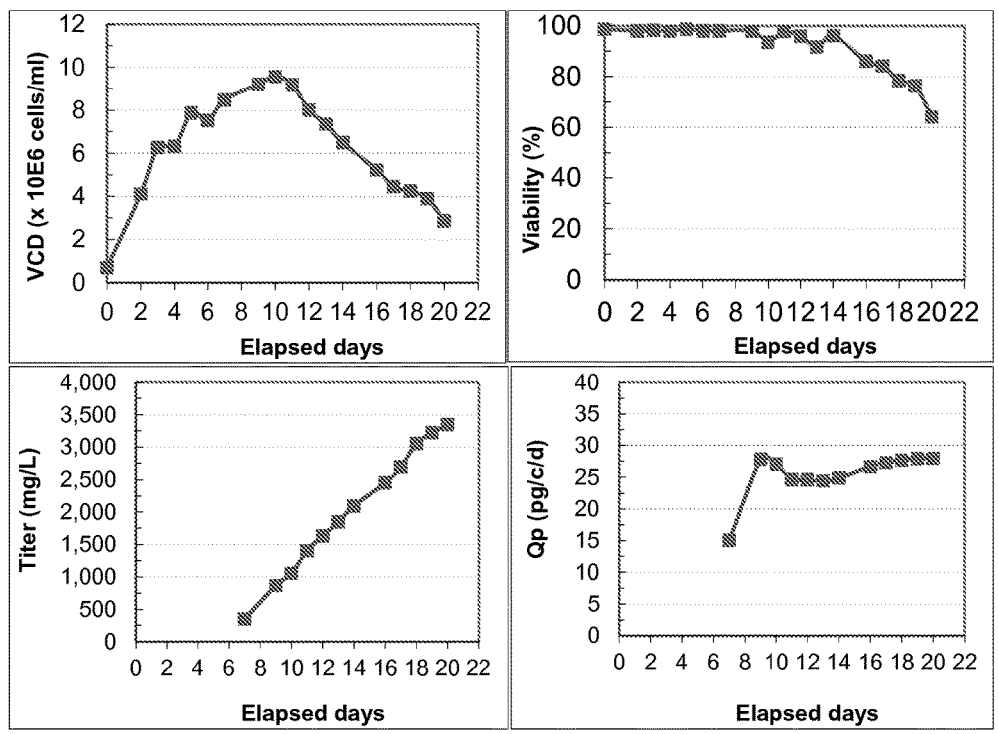
FIG. 3: Rapid stable cell line development using MaxCyte static and flow electroporation. A humanized mAb DNA plasmid was transfected into CHO-S cells using the CHO2 electroporation protocol on the MaxCyte STX. Limiting dilution cloning was carried out from the stable pool in G418 selection media. Cell lines were generated at week 6 and scaled up for production and accession cell bank. Productivity is >3 g/L as a fed batch.

Results in FIG. 3 shows the cell performance of one of the best stable clones. This cell line has robust cell growth and high viability during the production cultivation. Specific (~27 pg/c/d) and volumetric (>3 g/L) productivities were also high and very comparable and competitive to the stable cell lines generated by others equipped with many advanced technologies.

Figure 4:
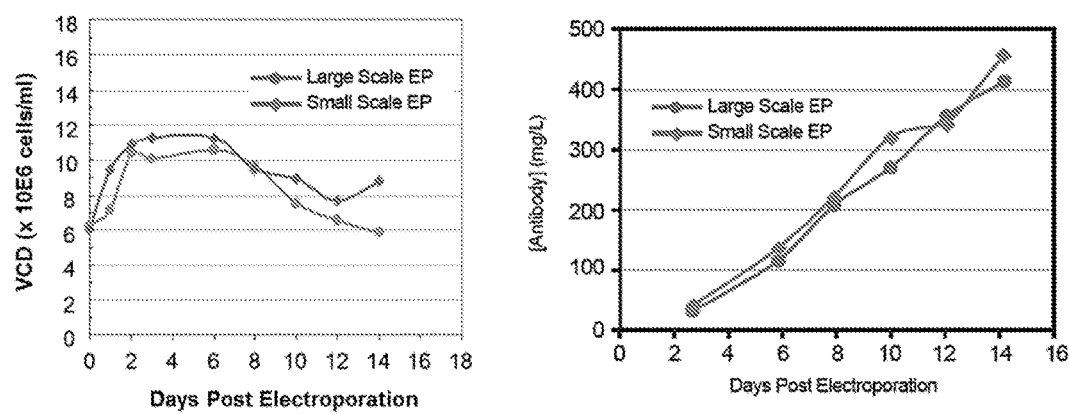
FIG. 4: High Titer Antibody Production.

The results in FIG. 4 demonstrate high titer antibody production with the methods of the current claims. $2.4 \times 10^8$ or $1 \times 10^{10}$ CHO cells were transfected with an antibody expression plasmid (1 μg DNA per $1 \times 10^6$ cells) using three small scale or a single large electroporation run on the MaxCyte STX respectively. Total IgG concentrations were measured on days 3-14 post EP. $1 \times 10^{10}$ CHO cells transfected using a single 30 minute electroporation run produced antibody yields of greater than 1 g from a 2.8 L culture (FIG. 4). The MaxCyte VLX has the capacity to transfect $2 \times 10^{11}$ cells in a single 30 minute run which if projected would equate to production of over 20 grams of antibody from a single transient transfection run.

Figure 5:
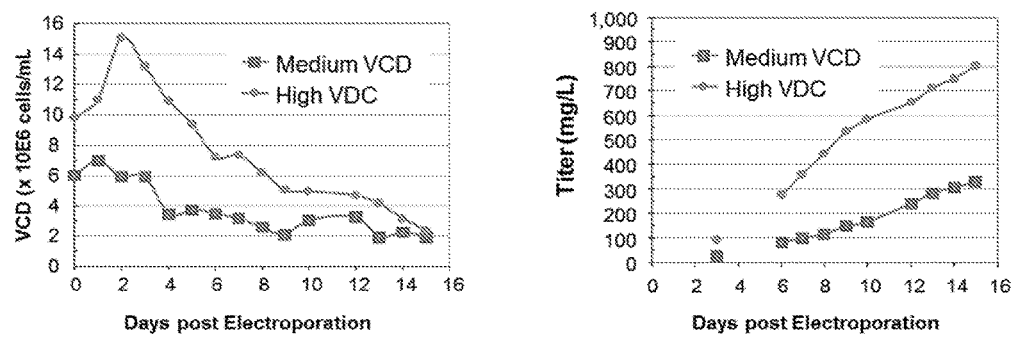
FIG. 5: Increasing Post Electroporation Cell Density Increases Secreted Antibody Titers.

$1 \times 10^{10}$ CHOs cells were harvested and resuspended at $2 \times 10^8$ cells/mL in 50% MaxCyte electroporation buffer. Cells were transiently transfected with an antibody expression plasmid (1 ug DNA/1E6 cells) by flow electroporation (EP) in a CL-2 processing assembly. Post EP, cells were inoculated into two shake flasks at densities of 6 million or 10 million cells per mL, respectively. Cultures were fed daily, 1 mM Na butyrate was added 24 hrs post EP and the culture temperature was lowered to 32° C. 24 hrs post EP (FIG. 5). The results of FIG. 5 demonstrate that increasing post electroporation cell density increases secreted antibody titers.

Figure 6:
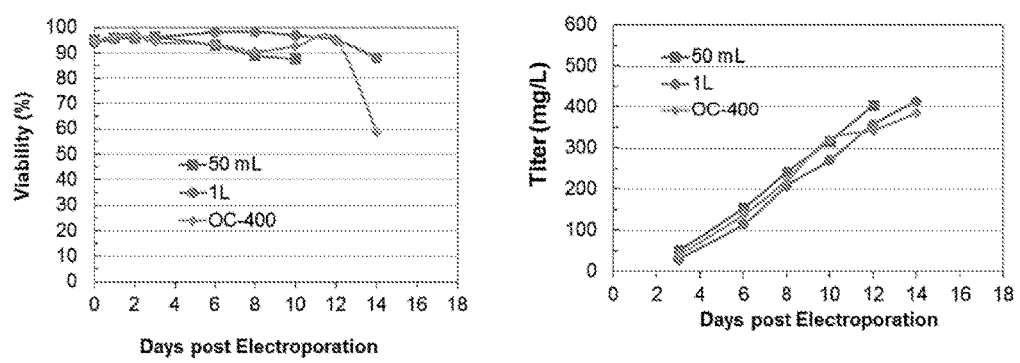
FIG. 6: Effect of different size culture flasks on antibody production.

To test the effect of different size culture flasks on antibody production, CHO cells were resuspended at 2×10e 8 cells/mL in 50% MaxCyte electroporation buffer. 1×10e10 or 2.4×10e8 cells were transiently transfected with an antibody expression plasmid (1 μg DNA/1x10e6 cells) in one CL-2 or 3 OC-400 PAs. respectively. Cells from the CL-2 were inoculated into two shake flasks containing 1 L or 50 mL of media, respectively; cells from the three OC-400s were combined and inoculated into 50 mL. Starting cell densities were the same in all three flasks. Cultures were fed daily, 1% Na butyrate was added 24 hrs post EP and the culture temperature was lowered to 32° C. 24 hrs post EP. Antibody titers were measured by ELISA. Comparable titers in all three flasks illustrate the scalability and reproducibility of MaxCyte's transfection technology (FIG. 6).

Figure 7:
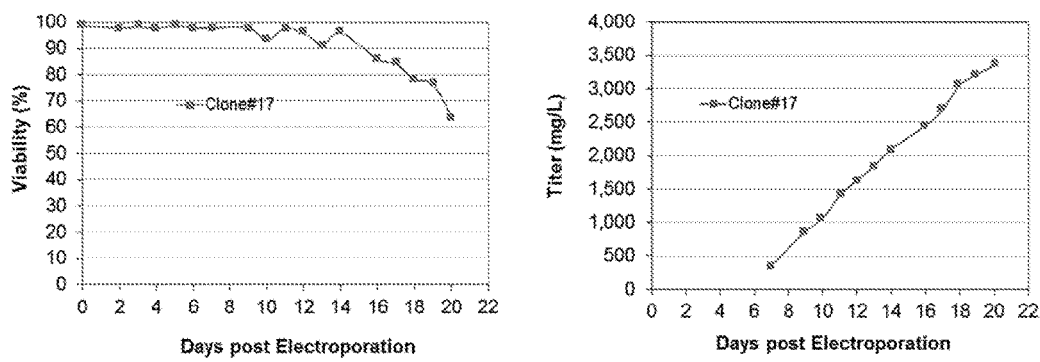
FIG. 7: Rapid stable cell line development using MaxCyte static and flow electroporation.

To demonstrate rapid stable cell line development using MaxCyte flow electroporation, a humanized mAb DNA was transfected into CHO-S cells by STX technology. Then, limiting dilution cloning was carried out from the stable pool in G418 selection media. Cell lines were generated at week 6 and scaled up for the production and accession cell bank. The production conditions were the same as transient expression. Productivity is >3 g/L as a fed batch (FIG. 7).

Figure 8:
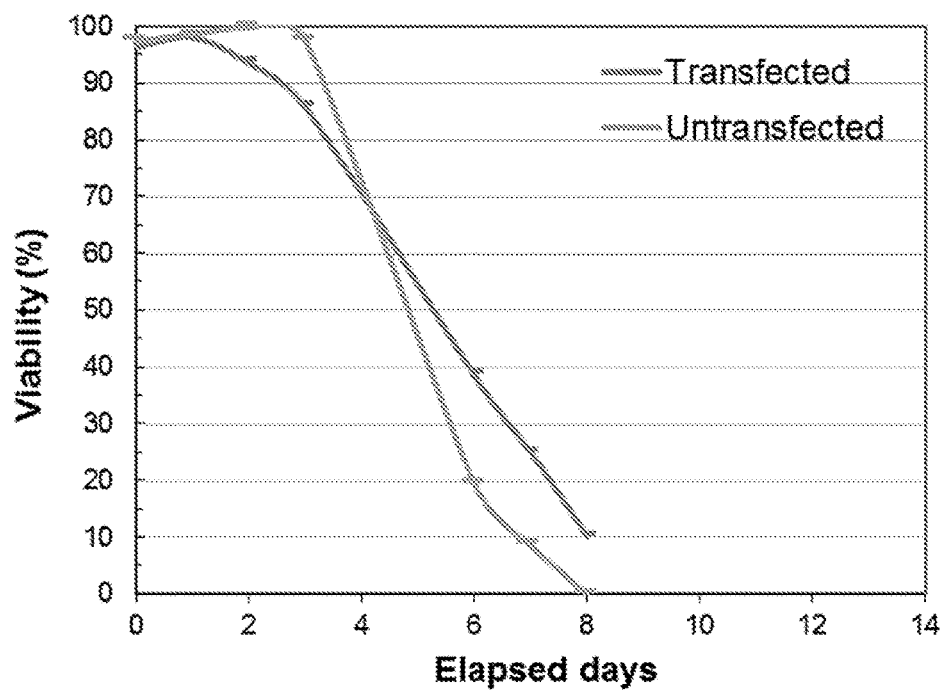
FIG. 8: Cell killing curve with G418 treatment.

FIG. 8 demonstrates a cell killing curve with G418 treatment, where Both transfected and Untransfected cells were treated with 1.6 g/L G418 24 hours post electroporation. Untransfected cells were completely killed at day 8 while transfected cells still have good amounts of viable transfected cells for limiting dilution cloning.

Table 1 summarizes the stable cell line process and results. Results indicated that clone formation efficiency was high (66%). Only 479 clones were screened and high expressing stable cell line (>3 g/L titer) was identified in about 8 weeks including an accession cell bank and a fed-batch culture. Other methods necessitate the need to screen several thousand clones with advanced instruments like automated liquid handling system, and high throughput screening and selection by ClonePix and FACS sorting methods to identify a clone with 1-4 g/L productivity in about 4-6 months or more. Using MaxCyte STX technology has clear advantages for the stable cell line development in terms of the capital equipment cost, employee resource investment and tight timeline of the project management.

In conclusion, MaxCyte STX technology can develop high expressing stable cell lines for drug development as a rapid, efficient, cost-effective and proprietary free manner with a unique high stringent selection process. It shortens selection process, reduces cell handling and labor cost, provides high selection success rate, and doesn't require any advanced technology like automation of liquid handling and stable clone selection system/platform. So MaxCyte's transfection technology facilitates rapid progression of the drug development through pre-clinical studies in to clinical trials with the same high expressing stable cell line which will dramatically reduce the cost and shorten the timeline of the product development. It will be a great tool for the biopharmaceutical drug development.

TABLE 1

Summary of stable CHO cell line development.

| Selection & Screening | Linearized DNA |
|---|---|
| 96-well plate | 25 |
| Seed cell density | 0.3 cell/well |
| No. of screened clones | 479 |
| Efficiency of clone formation | 66% |
| No. & percentage of evaluated top clones | 53 and 11% |
| The productivity of the best clone | 3 g/L |
| Time of a stable cell line development (included a small batch and accession cells bank) | ~8 weeks |

Example 2—Stable Cell Line Generation with Maxcyte STX Technology

Maxcyte STX Technology provides for a fast and cost effective platform to generate stable and high producer cell lines for recombinant protein production. An exemplary protocol of stable cell line generation is described below.

CHOS cells are maintained in base media (CD CHO with 1× Glutamax and 1×HT solution) in linear log cell growth phase at a density of 1e6 to 4e6 cells/mL. Cells are split one day prior to transfection to a density of 2e6 cells/mL. On the day of transfection, cells at a density of 2e8 cells/mL can be electroporated with DNA (which can be linearized) at a concentration of 400 μg/mL with an electroporation buffer.

Cells are allowed to recover for 30-40 at 37° C. in 5% $CO_2$ in an incubator in a 250 mL Erlenmeyer flask. Following recovery, cells are suspended in 40 mL of base media and returned to culture with shaking One day post electroporation, cells are pelleted at 1200 RPM for 10 min. and resuspended in 40 mL of selection media (base media supplemented with 1× selection agent) to start selection. To determine the 1× selection agent concentration, a killing curve can be generated by treating untransfected cells with multiple concentrations of selection agent.

Cell killing may be stabilized after approximately two weeks in selection media and is usually indicated by sustained viability levels of 10-20%. At this point, a limiting dilution cloning process can be initiated in base media supplemented with 0.3× selection agent. Clones can be screened by ELISA after the initiation of colony formation. Highest producing clones can be retained for further evaluation using batch or fed batch cultures in 125 mL shake flasks to identify and select the best clones. Clones may then be expanded to generate a research cell bank.

All of the methods disclosed and claimed herein can be made and executed without undue experimentation in light of the present disclosure. While the compositions and methods of this invention have been described in terms of preferred embodiments, it will be apparent to those of skill in the art that variations may be applied to the methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

REFERENCES

The following references, to the extent that they provide exemplary procedural or other details supplementary to those set forth herein, are specifically incorporated herein by reference.

Carroll, et al., *Expert Opin Biol Ther.* 4(11):1821-9, 2004.
de la Cruz Edmonds, et al., *Mol Biotechnol.* 34(2):179-90, 2006.
Derouazi, et al., *Biotechnol Bioeng.* 87(4):537-45, 2004.
Dharshanan, et al., *Elec J Biotechnol.* 4(2), 2011.
Fan, et al., *Biotechnol Bioeng.* 109(4):1007-15, 2012.
Florea, et al., *AAPS PharmSci.* 4(3):E12, 2002.
Kim, et al., *BMC Biotechnol.* 12:24, 2012.
Lindgren, et al., *Cytotechnology.* 59(1):1-10, 2009.
Moses, et al., *Adv Biosci Biotechnol.* 3:918-927, 2012.
Nair, et al., *BMC Res Notes.* 4:178-85, 2011.
Naoko, et al., *Biotechnol Bioeng.* 87(15):614-22, 2004.
Reisinger, et al., *Cytotechnology.* 60(1-3):115-23, 2009.
Shi, et al., *J Vis Exp.* 55, 2011.
Sleiman, et al., *Biotechnol Bioeng.* 99(3):578-87, 2008.
Tait, et al., *Biotechnol Bioeng.* 88(6):707-21, 2004.
Thomas, et al., *JALA.* 13:145-51, 2008.

The invention claimed is:
1. A method for producing a stable mammalian cell line that expresses an exogenous polypeptide comprising:

transfecting an expression construct into cells using electroporation, wherein the expression construct comprises i) a selectable gene and ii) a sequence encoding an exogenous polypeptide;

selecting for expression of the selection gene in transfected cells under culture conditions comprising a conditionally lethal concentration of at least 1.6 mg/ml of G418 for at least 6 days.

2. The method of claim 1, wherein electroporation is flow electroporation.

3. The method of claim 1, wherein after the cells are cultured with G418 at a conditionally lethal concentration, cells are maintained in culture having a lower concentration of the antibiotic, wherein the lower concentration is about 25% to 75% of the conditionally lethal concentration.

4. The method of claim 3, wherein the lower concentration is no more than about 50% of the conditionally lethal concentration.

5. The method of claim 3, wherein cells are maintained at the lower concentration for 4 to 20 days.

6. The method of claim 1, wherein the cells are CHO cells.

7. The method of claim 1, wherein the culture conditions comprise sodium butyrate.

8. The method of claim 1, further comprising expanding a clonal isolated and selected cell to produce clonal cells expressing the exogenous polypeptide; wherein expanding a clonal isolated cell is in media comprising G418; and wherein the concentration of G418 during expansion is no more than 50% of the conditionally lethal concentration of G418.

9. The method of claim 1, further comprising expanding a clonal isolated and selected cell to produce clonal cells expressing the exogenous polypeptide, wherein the cells are expanded in media comprising G418; and wherein the concentration of G418 is at a conditionally lethal concentration.

10. The method of claim 1, further comprising isolating or purifying the exogenous polypeptide produced by the cells; wherein at least 1.0 g/L of exogenous polypeptide is purified.

11. The method of claim 1, further comprising expanding a clonal isolated and selected cell to produce clonal cells expressing the exogenous polypeptide, wherein the expanded clonal cells produce at least about 1.5 g/L of exogenous polypeptide within 8 weeks of being transfected.

12. A method for producing a stable CHO cell expressing line comprising:
    a) transfecting into CHO cells an expression construct comprising a sequence i) encoding a polypeptide conferring G418 resistance and ii) encoding an exogenous polypeptide using a flow electroporation device;
    b) selecting transfected CHO cells in media comprising at least 1.6 mg/ml of G418 for at least 6 days;
    c) isolating selected transfected CHO cells by limiting dilution to obtain clonal cells; and,
    d) expanding isolated transfected CHO cells to produce a stable CHO cell expressing line.

13. A method for screening for high producing CHO cell lines comprising:
    a) transfecting into CHO cells an expression construct comprising a sequence i) encoding a polypeptide conferring G418 resistance and ii) encoding an exogenous polypeptide using a flow electroporation device;
    b) selecting transfected CHO cells in media comprising greater than about 1.6 mg/ml of G418 for at least 6 days;
    c) isolating selected transfected CHO cells by limiting dilution to obtain clonal cells;
    d) expanding isolated transfected CHO cells to produce a stable CHO cell expressing line; and,
    e) evaluating the cells for production of the exogenous polypeptide.

14. The method of claim 13, wherein the media in b) is serum-free media.

* * * * *